US007035795B2

(12) United States Patent
Burnett et al.

(10) Patent No.: US 7,035,795 B2
(45) Date of Patent: Apr. 25, 2006

(54) SYSTEM AND METHOD FOR CHARACTERIZING VOICED EXCITATIONS OF SPEECH AND ACOUSTIC SIGNALS, REMOVING ACOUSTIC NOISE FROM SPEECH, AND SYNTHESIZING SPEECH

(75) Inventors: Greg C. Burnett, Livermore, CA (US); John F. Holzrichter, Berkeley, CA (US); Lawrence C. Ng, Danville, CA (US)

(73) Assignee: The Regents of the University of California, Oakland, CA (US)

( * ) Notice: Subject to any disclaimer, the term of this patent is extended or adjusted under 35 U.S.C. 154(b) by 314 days.

(21) Appl. No.: 10/682,786

(22) Filed: Oct. 8, 2003

(65) Prior Publication Data

US 2004/0083100 A1 Apr. 29, 2004

Related U.S. Application Data

(60) Continuation of application No. 09/851,550, filed on May 8, 2001, now Pat. No. 6,711,539, which is a division of application No. 09/433,453, filed on Nov. 4, 1999, now Pat. No. 6,377,919, which is a continuation-in-part of application No. 08/597,596, filed on Feb. 6, 1996, now Pat. No. 6,006,175.

(60) Provisional application No. 60/120,799, filed on Feb. 19, 1999.

(51) Int. Cl.
*G10L 21/02* (2006.01)

(52) U.S. Cl. ...................................... 704/223; 704/226

(58) Field of Classification Search ................ 704/223, 704/226
See application file for complete search history.

(56) References Cited

U.S. PATENT DOCUMENTS

| 4,401,855 | A | * | 8/1983 | Broderson et al. | .......... 704/219 |
| 4,862,503 | A | * | 8/1989 | Rothenberg | .................. 704/235 |
| 4,959,865 | A | * | 9/1990 | Stettiner et al. | ............ 704/233 |
| 5,171,930 | A | * | 12/1992 | Teaney | ........................ 84/725 |
| 5,251,261 | A | * | 10/1993 | Meyer et al. | ................ 704/211 |
| 5,326,349 | A | * | 7/1994 | Baraff | ............................ 623/9 |
| 5,454,375 | A | * | 10/1995 | Rothenberg | ................. 600/538 |

(Continued)

OTHER PUBLICATIONS

Kent et al, "The Acoustic Analysis of Speech", 1992 Singular Publishing Group, pp. 80-85.*

*Primary Examiner*—Wayne Young
*Assistant Examiner*—Michael N. Opsasnick
(74) *Attorney, Agent, or Firm*—Eddie E. Scott; Alan H. Thompson; Lloyd E. Dakin, Jr.

(57) ABSTRACT

The present invention is a system and method for characterizing human (or animate) speech voiced excitation functions and acoustic signals, for removing unwanted acoustic noise which often occurs when a speaker uses a microphone in common environments, and for synthesizing personalized or modified human (or other animate) speech upon command from a controller. A low power EM sensor is used to detect the motions of windpipe tissues in the glottal region of the human speech system before, during, and after voiced speech is produced by a user. From these tissue motion measurements, a voiced excitation function can be derived. Further, the excitation function provides speech production information to enhance noise removal from human speech and it enables accurate transfer functions of speech to be obtained. Previously stored excitation and transfer functions can be used for synthesizing personalized or modified human speech. Configurations of EM sensor and acoustic microphone systems are described to enhance noise cancellation and to enable multiple articulator measurements.

3 Claims, 13 Drawing Sheets

U.S. PATENT DOCUMENTS

| | | | |
|---|---|---|---|
| 5,473,726 A * | 12/1995 | Marshall | 704/231 |
| 5,522,013 A * | 5/1996 | Vanska | 704/255 |
| 5,528,726 A * | 6/1996 | Cook | 704/261 |
| 5,573,012 A * | 11/1996 | McEwan | 600/595 |
| 5,659,658 A * | 8/1997 | Vanska | 704/261 |
| 5,668,925 A * | 9/1997 | Rothweiler et al. | 704/220 |
| 5,717,828 A * | 2/1998 | Rothenberg | 704/251 |
| 5,794,203 A * | 8/1998 | Kehoe | 704/271 |
| 6,081,776 A * | 6/2000 | Grabb et al. | 704/219 |
| 6,240,386 B1 * | 5/2001 | Thyssen et al. | 704/220 |
| 6,411,925 B1 * | 6/2002 | Keiller | 704/200 |
| 6,415,253 B1 * | 7/2002 | Johnson | 704/210 |
| 6,526,139 B1 * | 2/2003 | Rousell et al. | 376/406.03 |
| 6,526,376 B1 * | 2/2003 | Villette et al. | 704/207 |
| 6,560,575 B1 * | 5/2003 | Keiller | 704/241 |

\* cited by examiner

SYSTEM AND METHOD FOR CHARACTERIZING VOICED EXCITATIONS OF SPEECH AND ACOUSTIC SIGNALS, REMOVING ACOUSTIC NOISE FROM SPEECH, AND SYNTHESIZING SPEECH

CROSS-REFERENCE TO RELATED APPLICATIONS

This application is a continuation of U.S. patent application Ser. No. 09/851,550 filed May 8, 2001 (Now U.S. Pat. No. 6,711,539 issued Mar. 23, 2004), which was a division of U.S. patent application Ser. No. 09/433,453 filed Nov. 4, 1999 (Now U.S. Pat. No. 6,377,919 issued Apr. 23, 2002), which was a continuation-in-part of U.S. patent application Ser. No. 08/597,596 entitled "Methods and Apparatus for Non-Acoustic Speech Characterization and Recognition," filed on Feb. 6, 1996, by John F. Holzrichter (Now U.S. Pat. No. 6,006,175 issued Dec. 21, 1999).

This application relates to and incorporates herein by reference U.S. patent application Ser. No. 09/205,159 "System and Method for Characterizing, Synthesizing, and/or Canceling Out Acoustic Signals From Inanimate Sound Sources" filed on Dec. 2, 1998, by Burnett et al. (Now U.S. Pat. No. 6,542,857 issued Apr. 1, 2003), and U.S. Pat. No. 5,729,694 entitled "Speech Coding, Reconstruction and Recognition Using Acoustics and Electromagnetic Waves," issued on Mar. 17, 1998 by Holzrichter et al. These related applications are commonly assigned to The Regents of the University of California, located in Oakland, Calif.

REFERENCE TO PROVISIONAL APPLICATION TO CLAIM PRIORITY

A priority date for this present U.S. patent application has been established by prior U.S. Provisional Patent Application Ser. No. 60/120,799, entitled "System and Method for Characterization of Excitations, for Noise Removal, and for Synthesizing Human Speech Signals," filed on Feb. 19, 1999 by inventors Greg C. Burnett et al.

This application relates to and incorporates herein by reference U.S. patent application Ser. No. 09/205,159 "System and Method for Characterizing, Synthesizing, and/or Canceling Out Acoustic Signals From Inanimate Sound Sources" filed on Dec. 2, 1998, by Burnett et al., and U.S. Pat. No. 5,729,694 entitled "Speech Coding, Reconstruction and Recognition Using Acoustics and Electromagnetic Waves," issued on Mar. 17, 1998 by Holzrichter et al. These related applications are commonly assigned to The Regents of the University of California, located in Oakland, Calif.

The United States Government has rights in this invention pursuant to Contract No. W-7405-ENG-48 between the United States Department of Energy and the University of California for the operation of Lawrence Livermore National Laboratory.

BACKGROUND OF THE INVENTION

1. Field of the Invention

The present invention relates generally to systems and methods for automatically describing human speech, and more particularly to systems and methods for characterizing voiced excitations of speech and acoustic signals, removing acoustic noise from speech, and synthesizing human/animate speech.

2. Discussion of Background Art

Sound characterization, simulation, and noise removal relating to human speech is a very important ongoing field of research and commercial practice. Use of EM sensors and acoustic microphones for purposes of human speech characterization has been described in the referenced application Ser. No. 08/597,596 to the U.S. patent office, which is incorporated herein by reference. Said patent application describes methods by which EM sensors can measure positions versus time of human speech articulators, along with substantially simultaneous measured acoustic speech signals for purposes of
more accurately characterizing each segment of human speech. Furthermore, the said patent application describes valuable applications of said EM sensor and acoustic methods for purposes of improved speech recognition, coding, speaker verification, and other applications.

A second related U.S. patent issued on Mar. 17, 1998 as U.S. Pat. No. 5,729,694, titled "Speech Coding, Reconstruction and Recognition Using Acoustics and Electromagnetic Waves," by J. F. Holzrichter and L. C. Ng is also incorporated herein by reference. Patent '694 describes methods by which speech excitation functions of human (or similar animate objects) are characterized using EM sensors, and the substantially simultaneously acoustic speech signal is then characterized using generalized signal processing technique. The excitation characterizations described in '694, as well as in application Ser. No. 08/597,596, rely on associating experimental measurements of glottal tissue interface motions with models to determine an air pressure or airflow excitation function. The measured glottal tissue interfaces include vocal folds, related muscles, tendons, cartilage, as well as, sections of a windpipe (e.g. glottal region) directly below and above the vocal folds.

The described procedures in application Ser. No. 08/597,596, enable new and valuable methods for characterizing the substantially simultaneously measured acoustic speech signal, by using the non-acoustic EM signals from the articulators and acoustic structures as additional information. Those procedures use the excitation information, other articulator information, mathematical transforms, and other numerical methods, and describes the formation of feature vectors of information that numerically describe each speech unit, over each defined time frame using the combined information. This characterizing speech information is then related to methods and systems, described in said patents and applications, for improving speech application technologies such as speech recognition, speech coding, speech compression, synthesis, and many others.

Another important patent application that is herein incorporated by reference is U.S. patent Ser. No. 09/205,159 entitled "System and Method for Characterizing, Synthesizing, and/or Canceling Out Acoustic Signals From Inanimate Sound Sources," filed on Dec. 2, 1998 by G. C. Burnett, J. F. Holzrichter, and L. C. Ng. This invention application relates generally to systems and methods for characterizing, synthesizing, and/or canceling out acoustic signals from inanimate sound sources, and more particularly for using electromagnetic and acoustic sensors to perform such tasks.

Existing acoustic speech recognition systems suffer from inadequate information for recognizing words and sentences with high probability. The performance of such systems also drops rapidly when noise from machines, other speakers, echoes, airflow, and other sources are present.

In response to the concerns discussed above, what is needed is a system and method for automated human speech that overcomes the problems of the prior art. The inventions herein describe systems and methods to improve speech recognition and other related speech technologies.

SUMMARY OF THE INVENTION

The present invention is a system and method for characterizing voiced speech excitation functions (human or animate) and acoustic signals, for removing unwanted acoustic noise from a speech signal which often occurs when a speaker uses a microphone in common environments, and for synthesizing personalized or modified human (or other animate) speech upon command from a controller.

The system and method of the present invention is particularly advantageous because a low power EM sensor detects tissue motion in a glottal region of a human speech system before, during, and after voiced speech. This is easier to detect than a glottis itself. From these measurements, a human voiced excitation function can be derived. The EM sensor can be optimized to measure sub-millimeter motions of wall tissues in either a sub-glottal or supra-glottal region (i.e., below or above vocal folds), as vocal folds oscillate (i.e., during a glottal open close cycle). Motions of the sub-glottal wall or supra-glottal wall provide information on glottal cycle timing, on air pressure determination, and for constructing a voiced excitation function. Herein, the terms glottal EM sensor and glottal radar and GEMS (i.e., glottal electromagnetic sensor) are used interchangeably.

Air pressure increases and decreases in the sub-glottal region, as vocal folds close (obstructing airflow) and then open again (enabling airflow), causing the sub-glottal walls to expand and then contract by dimensions ranging from <0.1 mm up to 1 mm. In particular, a rear wall (posterior) section of a trachea is observed to respond directly to increases in sub-glottal pressure as vocal folds close. Timing of air pressure increase is directly related to vocal fold closure (i.e., glottal closure). Herein "trachea" and "sub-glottal windpipe" refer to a same set of tissues. Similarly, supra-glottal walls in a pharynx region, expand and contract, but in opposite phase to sub-glottal wall motion. For this document "pharynx" and the "supra-glottal region" are synonyms; also, "time segment" and "time frame" are synonyms.

Methods of the present invention describe how to obtain an excitation function by using a particular tissue motion associated with glottis opening and closing. These are wall tissue motions, which are measured by EM sensors, and then associated with air pressure versus time. This air pressure signal is then converted to an excitation function of voiced speech, which can be parameterized and approximated as needed for various applications. Wall motions are closely associated with glottal opening and closing and glottal tissue motions.

The windpipe tissue signals from the EM sensor also describe periods of no speech or of unvoiced speech. Using the statistics of the user's language, the user of these methods can estimate, to a high degree of certainty, time periods wherein no vocal-fold motion means time periods of no speech, and time periods where unvoiced speech is likely. In addition, unvoiced speech presence and qualities can be determined using information from the EM sensor measuring glottal region wall motion, from a spectrum of a corresponding acoustic signal, and (if used) signals from other EM sensors describing processes of vocal fold retraction, or pharynx diameter enlargement, jaw motions, or similar activities.

The EM sensor signals that describe vocal tract tissue motions can also be used to determine acoustic signals being spoken. Vocal tract tissue walls (e.g., pharynx or soft palate), and/or tissue surfaces (e.g., tongue or lips), and/or other tissue surfaces connected to vocal tract wall-tissues (e.g., neck-skin or outer lip surfaces), vibrate in response to acoustic speech signals that propagate in the vocal tract. The EM sensors described in the '596 patent and elsewhere herein, and also methods of tissue response-function removal, enable determination of acoustic signals.

The invention characterizes qualities of a speech environment, such as background noise and echoes from electronic sound systems, separately from a user's speech so as to enable noise and echo removal. Background noise can be characterized by its amplitude versus time, its spectral content over determined time frames, and the correlation times with respect to its own time sequences and to the user's acoustic and EM sensed speech signals. The EM sensor enables removal of noise signals from voiced and unvoiced acoustic speech. EM sensed excitation functions provide speech production information (i.e., amplitude versus time information) that gives an expected continuity of a speech signal itself. The excitation functions also enable accurate methods for acoustic signal averaging over time frames of similar speech and threshold setting to remove impulsive noise. The excitation functions also can employ "knowledge filtering" techniques (e.g., various model-based signal processing and Kalman filtering techniques) and remove signals that don't have expected behavior in time or frequency domains, as determined by either excitation or transfer functions. The excitation functions enable automatic setting of gain, threshold testing, and normalization levels in automatic speech processing systems for both acoustic and EM signals, and enable obtaining ratios of voiced to unvoiced signal power levels for each individual user. A voiced speech excitation signal can be used to construct a frequency filter to remove noise, since an acoustic speech spectrum is restricted by spectral content of its corresponding excitation function. In addition, the voiced speech excitation signal can be used to construct a real time filter, to remove noise outside of a time domain function based upon the excitation impulse response. These techniques are especially useful for removing echoes or for automatic frequency correction of electronic audio systems.

Using the present invention's methods of determining a voiced excitation function (including determining pressure or airflow excitation functions) for each speech unit, a parameterized excitation function can be obtained. Its functional form and characteristic coefficients (i.e., parameters) can be stored in a feature vector. Similarly, a functional form and its related coefficients can be selected for each transfer function and/or its related real-time filter, and then stored in a speech unit feature vector. For a given vocabulary and for a given speaker, feature vectors having excitation, transfer function, and other descriptive coefficients can be formed for each needed speech unit, and stored in a computer memory, code-book, or library.

Speech can be synthesized by using a control algorithm to recall stored feature vector information for a given vocabulary, and to form concatenated speech segments with desired prosody, intonation, interpolation, and timing. Such segments can be comprised of several concatenated speech units. A control algorithm, sometimes called a text-to-speech algorithm, directs selection and recall of feature vector information from memory, and/or modification of information needed for each synthesized speech segment. The text-to-speech algorithm also describes how stored information can be interpolated to derive excitation and transfer function or filter coefficients needed for automatically constructing a speech sequence.

The present invention's method of speech synthesis, in combination with measured and parameterized excitation functions and a real time transfer function filter for each speech unit, as described in U.S. patent office application Ser. No. 09/205,159 and in U.S. patent '694 enables prosodic and intonation information to be applied to a synthesized speech sequences easily, enables compact storage of speech units, and enables interpolation of one sound unit to another unit, as they are formed into smoothly changing speech unit sequences. Such sequences are often comprised of phones, diphones, triphones, syllables, or other patterns of speech units.

These and other aspects of the invention will be recognized by those skilled in the art upon review of the detailed description, drawings, and claims set forth below.

DETAILED DESCRIPTION OF THE PREFERRED EMBODIMENT

Figure 1:
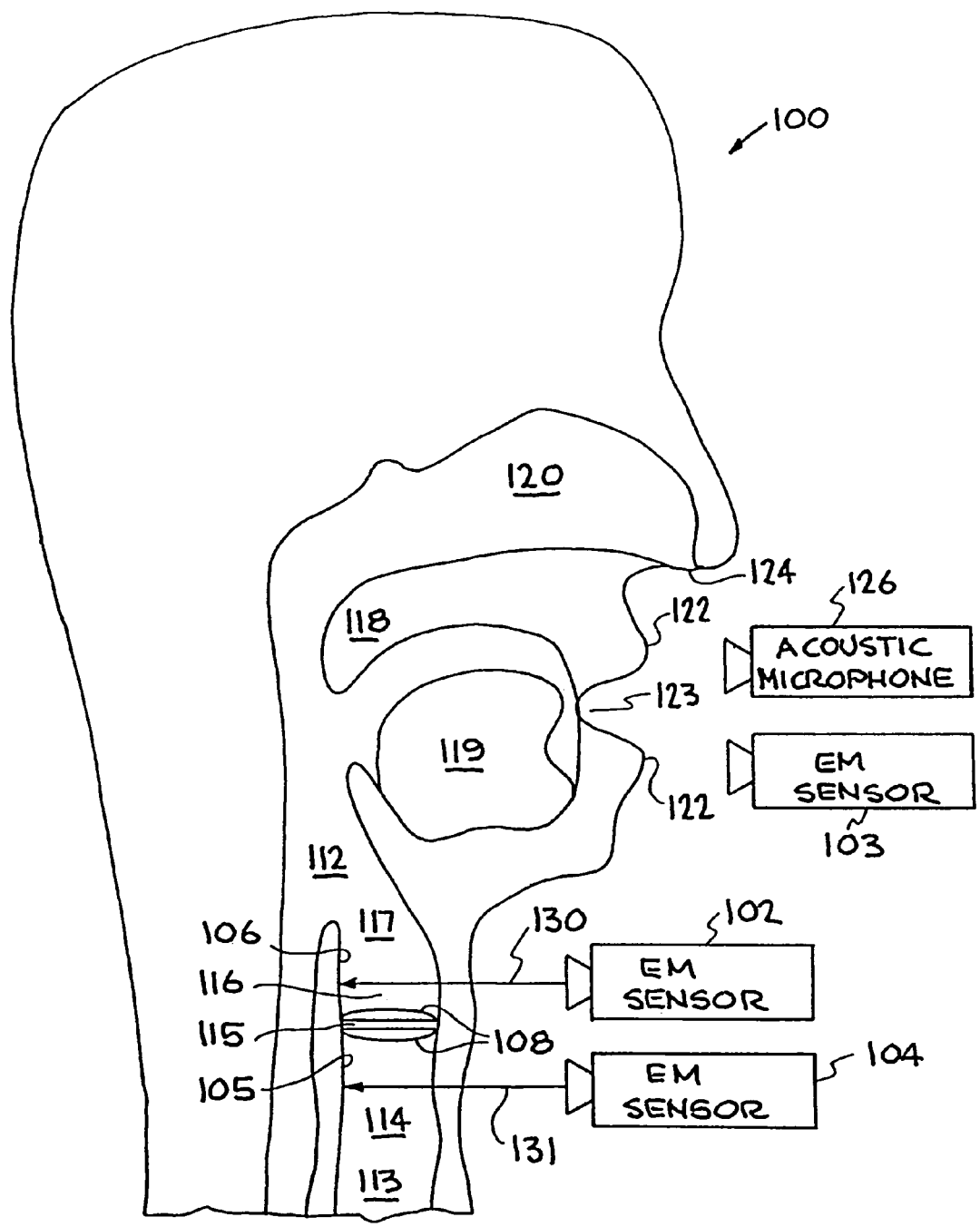
FIG. 1 is a pictorial diagram of positioning of EM sensors for measuring glottal region wall motions.

FIG. 1 is a pictorial diagram 100 of positioning of EM sensors 102 and 104 for measuring motions of a rear trachea wall 105 and a rear supra-glottal wall 106. These walls 105, 106 are also called windpipe walls within this specification. A first EM sensor 102 measures a position versus time (herein defined as motions) of the rear supra-glottal wall 106 and a second EM sensor 104 measures a position versus time of the rear tracheal wall 105 of a human as voiced speech is produced. Together or separately these sensors 102 and 104 form a micro-power EM sensor system. During voiced speech, vocal folds 108 open and close causing airflow and air pressure variations in a lower windpipe 113 and vocal tract 112, as air exits a set of lungs (not shown) and travels the lower windpipe 113 and vocal tract 112. Herein this process of vocal fold 108 opening and closing, whereby impulses of airflow and impulses of pressure excite the vocal tract 112, is called phonation. Air travels through the lower windpipe 113, passing a sub-glottal region 114 (i.e. trachea), and then passes through a glottal opening 115 (i.e. a glottis). Under normal speech conditions, this flow causes the vocal folds 108 to oscillate, opening and closing. Upon leaving the glottis 115, air flows into a supra-glottal region 116 just above vocal folds 108, and passes through a pharynx 117, over a tongue 119, between a set of lips 122, and out a mouth 123. Often, some air travels up over a soft palate 118 (i.e. velum), through a nasal tract 120 and out a nose 124. A third EM sensor 103 and an acoustic microphone 126 can also be used to monitor mouth 123 and nose 124 related tissues, and acoustic air pressure waves.

Two preferred locations and directions 130 and 131 are shown for the EM sensors 102 and 104 to measure supra-glottal and sub-glottal windpipe tissue motions. As the vocal folds 108 close, air pressure builds up in the sub-glottal region 114 (i.e., trachea) expanding the lower windpipe 113 wall, especially the rear wall section 105 of the sub-glottal region. Air pressure then falls in the supra-glottal region 116, and there the wall contracts inward, especially the rear wall section 106. In a second phase of a phonation cycle, when the vocal folds 108 open, air pressure falls in the sub-glottal region 114 whereupon the trachea wall contracts inward, especially the rear wall 105, and in the supra-glottal region air pressure increases and the supra-glottal 116 wall expands, especially the rear wall, 106.

By properly designing the EM sensors 102 and 104 for responsiveness to motions of windpipe wall sections, which are at defined locations, such as the rear wall of the trachea just below the glottis 115, wall tissue motion can be measured in proportion to as air pressure increases and decreases. The EM sensors 102 and 104, data acquisition methodology, feature vector construction, time frame determination, and mathematical processing techniques are described in U.S. Pat. No. 5,729,694 entitled "Speech Coding, Reconstruction and Recognition Using Acoustics and Electromagnetic Waves," issued on Mar. 17, 1998, by Holzrichter et al., and in U.S. patent application Ser. No. 08/597,596, entitled "Methods and Apparatus for Non-Acoustic Speech Characterization and Recognition," filed on Feb. 6, 1996, by John F. Holzrichter; and in U.S. patent application Ser. No. 09/205,159 "System and Method for Characterizing, Synthesizing, and/or Canceling Out Acoustic Signals From Inanimate Sound Sources," filed on Dec. 2, 1998, by Burnett et al., and in U.S. Pat. No. 5,729,694.

In a preferred embodiment of the present invention, the EM sensors 102 and 104 are homodyne micro-power EM radar sensors. Exemplary homodyne micro-power EM radar sensors are described in U.S. Pat. No. 5,573,012 and in a continuation in part there to, 5,766,208, both entitled "Body Monitoring and imaging apparatus and method," by Thomas E. McEwan, and in U.S. Pat. No. 5,512,834 Nov. 12, 1996 entitled "Homodyne impulse radar hidden object locator," by Thomas E. McEwan, all of which are herein incorporated by reference.

The EM sensors 102 and 104 used for illustrative demonstrations of windpipe wall motions employ an internal pass-band filter that passes EM wave reflectivity variations that occur only within a defined time window. This window occurs over a time-duration longer than about 0.14 milliseconds and shorter than about 15 milliseconds. This leads to a suppression of a signal describing the absolute rest position of the rear wall location. A position versus time plot (see FIG. 2) of the EM sensor signals show up as AC signals (i.e., alternating current with no DC offset), since the signals are associated with amplitudes of relative motions with respect to a resting position of a windpipe wall section. A pressure pulsation in the sub- or supra-glottal regions 114, 116, and consequent wall motions, are caused by the vocal folds 108 opening and closing. This open and closing cycle, for normal or "modal" speech, ranges from about 70 Hz to several hundred Hz. These wall motions occur in a time window and corresponding frequency band-pass of the EM sensors.

Other, usually slower, motions such as blood pressure induced pulses in neck arteries, breathing induced upper chest motions, vocal fold retraction motions, and neck skin-to sensor distance changes are essentially undetected by the EM sensors, which are in the preferred embodiment filtered homodyne EM radar sensors.

The EM sensor is preferably designed to transmit and receive a 2 GHz EM wave, such that a maximum of sensor sensitivity occurs for motions of a rear wall of a trachea (or at the rear wall of the supra-glottal section) of test subjects. Small wall motions ranging from 0.01 to 1 millimeter are accurately detected using the preferred sensor as long as they take place within a filter determined time window. As described in the material incorporated by reference, many other EM sensor configurations are possible.

Figure 2:
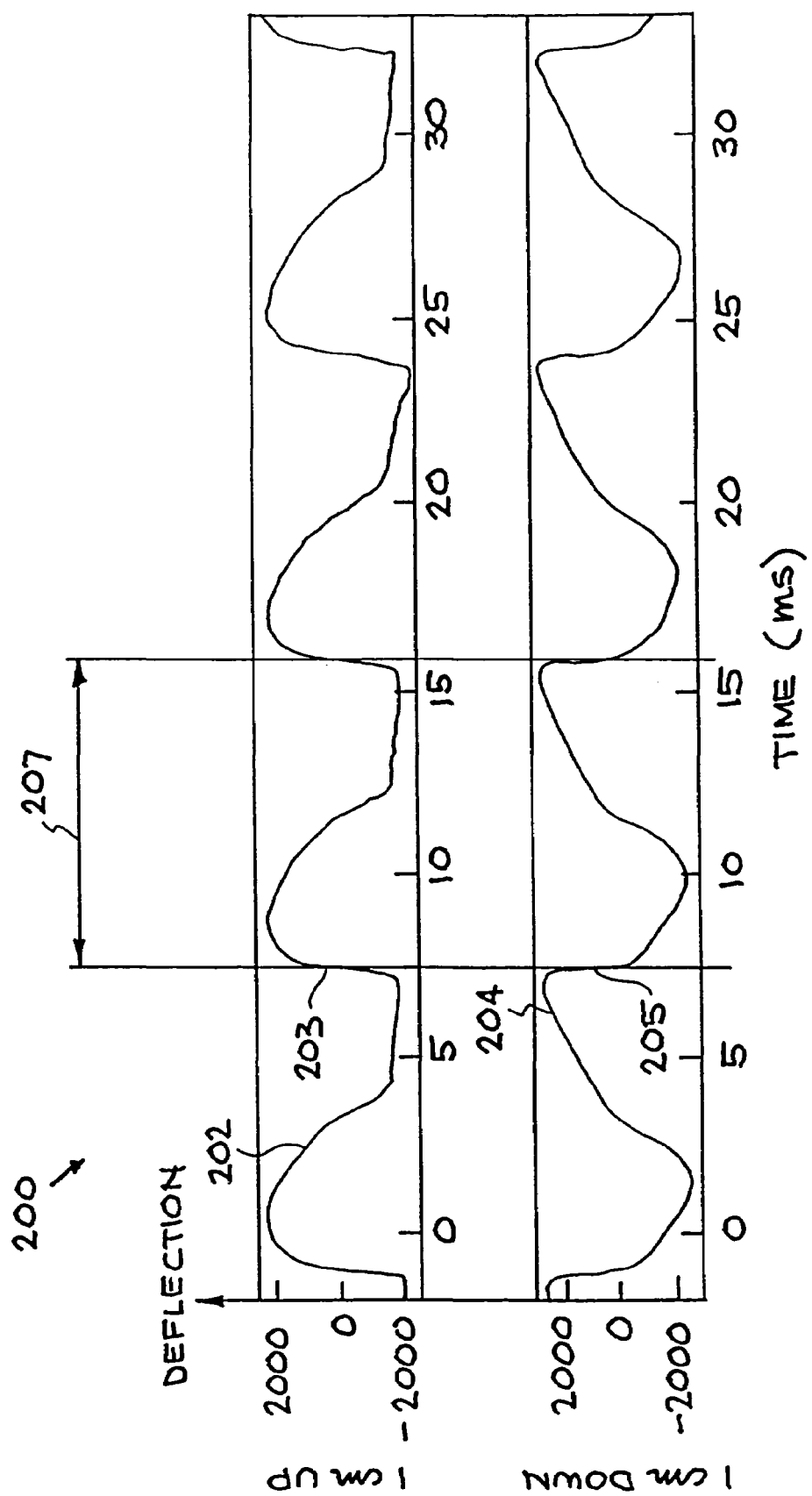
FIG. 2 is an exemplary graph of a supra-glottal signal and a sub-glottal signal over time as measured by the EM sensors.

FIG. 2 is an exemplary graph 200 of a supra-glottal signal 202 and a sub-glottal signal 204 over time as measured by the EM sensors 102 and 104 respectively. The supra-glottal signal 202 is obtained from wall tissue movements above the glottal opening 115 and the sub-glottal signal 204 is obtained from tracheal wall movements below the glottal opening 115. These signals represent motion of the walls of the windpipe versus time, and are related directly to local air pressure. Overall signal response time depends upon response time constants of the EM sensors 102 and 104 and time constants of the windpipe, which are due to inertial and other effects. One consequence is that the wall tissue motion is delayed with respect to sudden air pressure changes because of its slower response. Signal response time delays can be corrected with inverse filtering techniques, known to those skilled in the art.

In many applications, distinctions between airflow, U, and air pressure, P, are not used, since these functions often differ by a derivative in a time domain, P(t)=d/dt U(t), which is equivalent to multiplying U(t) by the frequency variable, ω, in frequency domain. This difference is automatically accommodated in most signal processing procedures (see Oppenheim et al.), and thus a distinction between airflow and air pressure is not usually important for most applications, as long as a consistent approach to using an excitation function is used, and approximations are understood.

Those skilled in the art will know that data obtained from the present invention enable various fluid and mechanical variables, such as fluid pressure P, velocity V, absolute tissue movement versus time, as well as, average tissue mass, compliance, and loss to be determined.

Most voiced signal energy is produced by rapid modulation of airflow caused by closure of the glottal opening 115. Lower frequencies of the supra-glottal signal 202 and the sub-glottal signal 204 play a minimal role in voice production. High frequencies 203 and 205 within the supra-glottal signal 202 and the sub-glottal signal 205 are caused by rapid closure of the glottis, which causes rapid tissue motions and can be measured by the EM sensors. For example, a rapidly opening and closing valve (e.g., a glottis) placed across a flowing air stream in a pipe will create a positive air pressure wave on one side of the valve equal to a negative air pressure wave on a other side of the valve if it closes rapidly with respect to characteristic airflow rates. In this way measurements of sub-glottal air pressure signals can be related to supra-glottal air pressure or to supra-glottal volume airflow excitation functions of voiced speech. The high frequencies generated by rapid signal changes 203 and 205 approximately equal the frequencies of a voiced excitation function as discussed herein and in U.S. Pat. No. 5,729,694. Associations between pressure and/or airflow excitations are not required for the preferred embodiment.

Speech-unit time-frame determination methods, described in those patents herein incorporated by reference, are used in conjunction with the supra-glottal signal 202 and the sub-glottal signal 204. A time of most rapid wall motion is associated with a time of most rapid glottal closure 203,205 is used to define a glottal cycle time 207, (i.e. a pitch period). "Glottal closure time" and "time of most rapid wall motion" are herein used interchangeably. As included by reference in co-pending U.S. patent application Ser. No. '596 and U.S. Pat. No. '694, a speech time frame can include time periods associated with one or more glottal time cycles, as well as, time periods of unvoiced speech or of no-speech.

Figure 3:
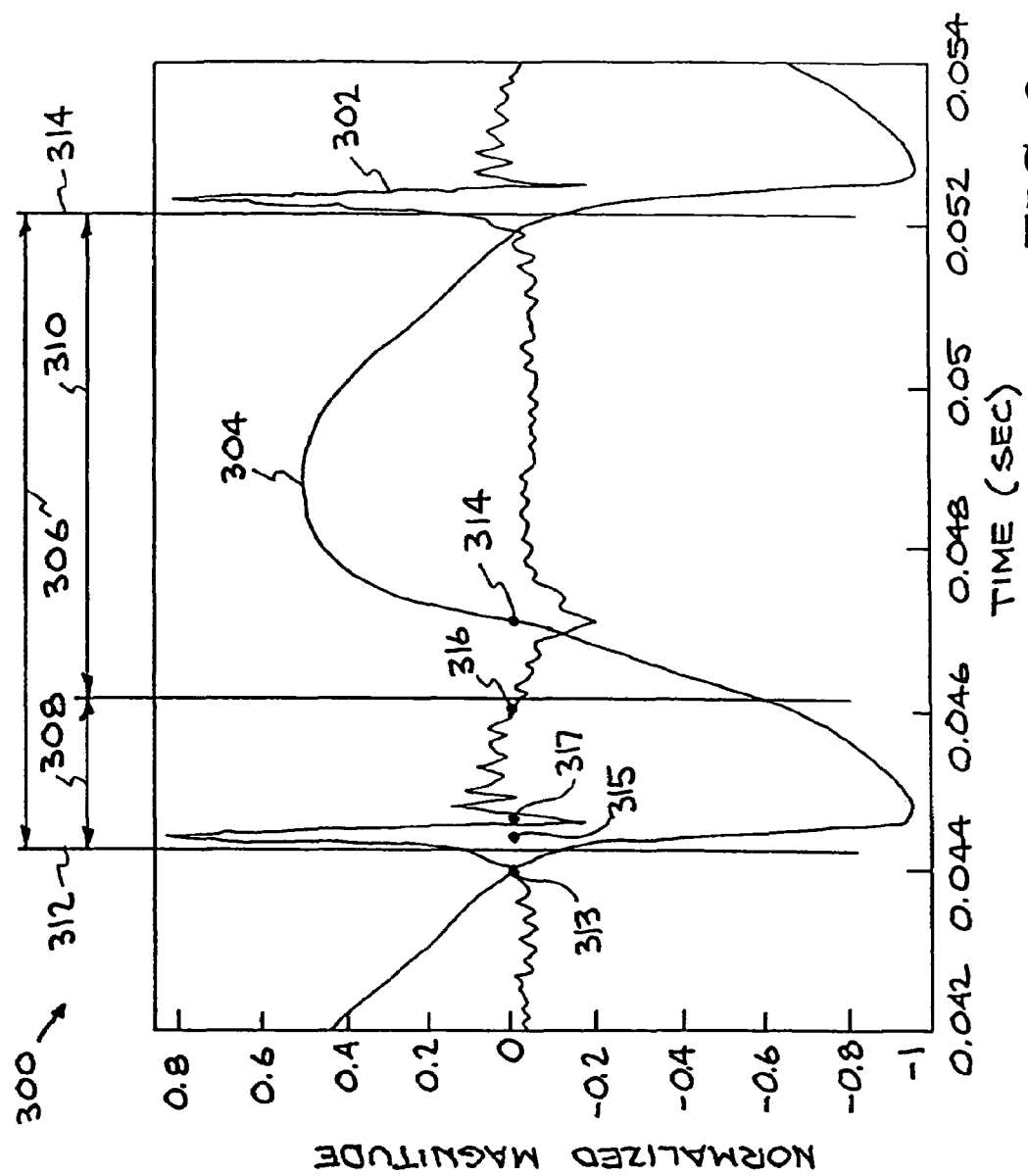
FIG. 3 is a graph of an EM sensor signal and a sub-glottal pressure signal versus time for an exemplary excitation function of voiced speech.

FIG. 3 is a graph 300 of an exemplary voiced speech pressure function 302 and an exemplary EM sensor signal representing an exemplary voiced speech excitation function 304 over a time frame from 0.042 seconds to 0.054 seconds. An exemplary glottal cycle 306 is defined by a method of most rapid positive change in pressure increase. The glottal cycle 306 includes a vocal fold closed time period 308 and a vocal fold-open time period 310.

The glottal cycle 306 begins with the vocal folds 108 closing just after a time 312 of 0.044 sec and lasts until the vocal folds open at a time 314 and close again at 0.052 seconds. A time of maximum pressure is approximated by a negative derivative time of the EM sensor signal.

Other glottal excitation signal characteristics can be used for timing, including times of EM sensor signal zero crossing (see FIG. 3 reference numbers 313 and 314), a time of peak pressure (see FIG. 3 reference numbers 315), a time of zero pressure (see FIG. 3 reference numbers 316), of minimum pressure (see FIG. 3 reference numbers 317), and times of maximum rate of change (see FIG. 3 reference numbers 312, 314) in either pressure increasing or pressure decreasing signals.

Seven methods for approximating a voiced speech excitation function (i.e., pressure excitation or airflow excitation of voiced speech) are numerically listed below. Each of the methods is based on an assumption that EM sensor signals have been corrected for internal filter and other distortions with respect to measured tissue motion signals, to a degree needed.

Excitation Method 1:

Define the voiced speech excitation function to be a negative of the measured sub-glottal wall tissue position signal 204, obtained using the EM sensors 104.

Excitation Method 2:

Define voiced speech excitation function to be measured supra-glottal wall tissue position signal 202, obtained using EM sensor 102.

Excitation Method 3:

Measure sub-glottal 114 or supra-glottal wall 116 positions versus time 104, 102 with an EM sensor. Correct EM sensor signals for mechanical responsiveness of wall tissue segments by removing wall segment inertia, compliance, and loss effects from EM sensor signals, using mechanical response functions, such as those describe in Ishizaka et al, IEEE Trans. on Acoustics, Speech and Signal Processing, ASSP-23 (4) August 1975. Obtain a representative air pressure function versus time 302. Define a negative of the sub-glottal pressure versus time 302 to be an excitation function. Alternatively, use supra-glottal EM sensor signal, determine supra-glottal pressure versus time, and define it to be the voiced excitation function. This method is further discussed in "The Physiological Basis of Glottal Electromagnetic Micro-power Sensors (GEMS) and their Use in Defining an Excitation Function for the Human Vocal Tract," by G. C. Burnett, 1999, (author's thesis at The University of California at Davis), available from "University Microfilms Inc." of Ann Arbor, Mich., document number 9925723.

Excitation Method 4:

Construct a mathematical model that describes airflow from lungs (e.g., using constant lung pressure) up through trachea 114, through glottis 115, up vocal tract 112, and out through the set of lips 122 or the nose 124 to the acoustic microphone 126. Use estimated model element values, and volume airflow estimates, to relate sub-glottal air pressure values to supra-glottal airflow or air pressure excitation function. One such mathematical model can be based upon electric circuit element analogies, as described in texts such as Flanagan, J. L., "Speech Analysis, Synthesis, and Perception," Academic Press, NY 1965, $2^{nd}$ edition 1972. Method 4 includes sub-steps of:

4.1) Starting with constant lung pressure and using formulae such as those shown in Flanagan, calculate an estimated volume airflow through the trachea to the sub-glottal region 114, then across the glottis 115, then into the supra-glottal section (e.g., pharynx) 117, up the vocal tract 112, to the velum 118, then over the tongue 119 and out the mouth 123, and/or through the velum 118, through the nasal passage 120, and out the nose 124, to the microphone 126. Calculate for several conditions of glottal area versus time.

4.2) Adjust lung pressure and element values in the mathematical model to agree with a measured sub-glottal 114 air pressure value 302 (given by EM sensor 104). Use EM sensor determined change in sub-glottal air pressure versus time (302) and the method 4.1 above to estimate airflow through the glottis opening 115 and into the supra-glottal region just above the glottis; and/or use the sub-glottal pressure and airflow to estimate supra-glottal 116 air pressure versus time.

4.3) Set the glottal airflow versus time to be equal to the voiced speech airflow excitation function, U. Alternatively, use model estimates for the supra-glottal pressure function and set equal to the voiced speech pressure excitation function, P.

Excitation Method 5:

5.1) Obtain a parameterized excitation functional (using time or frequency domain techniques). Find a shape of the excitation functional, by prior experiments and analysis, to resemble most voiced excitation functions needed for an application.

5.2) Adjust parameters of the parameterized functional to fit the shape of the excitation function.

5.3) Use the parameters of the functional to define the determined excitation function.

Excitation Method 6:

6.1) Insert airflow and/or air pressure calibration instruments between the lips 122 and/or into the nose 124 over the velum 118 and then into the supra-glottal region 116 or sub-glottal region 114. Alternatively, insert airflow and/or air pressure sensors through hypodermic needles inserted through the neck tissues, and into the sub-glottal 114 or supra-glottal 116 spatial regions.

6.2) Calibrate one or more EM sensors 102,104 and their signals 202,204 versus time, as a representative number of speech units and/or speech segments are spoken, against substantially simultaneous signals from the airflow and/or air pressure sensors.

6.3) Establish a mathematical (e.g., polynomial, numerical, differential or integral, or other) functional relationship between one or more measured EM sensor signals 202, 204 and one or more corresponding calibration signals.

6.4) Using the mathematical relationship determined in step 6.3, convert the measured EM sensor signals 202, 204 into a supra-glottal airflow or air pressure voiced excitation function.

6.5) Parameterize the excitation, as in 5.1 through 5.3, as needed.

Excitation Method 7:

Define a pressure excitation function by taking time derivative of an EM sensor measured signal of wall tissue motion. This approximation is effective because over a short time period of glottal closure, <1 ms, tracheal wall tissue effectively integrates fast impulsive pressure changes.

Acoustic Signal Functions

In preferred embodiment, the acoustic signal is measured using a conventional microphone. However, methods similar to those used to determine an excitation function (e.g., excitation methods 2, 3, 6 and 7) can be used to determine an acoustic speech signal function as it is formed and propagated out of the vocal tract to a listener. Exemplary EM sensors in FIG. 1, 102 and 103, using electromagnetic waves, with wavelengths ranging from meter to micrometers, can measure the motions of vocal tract surface tissues in response to air pressure pulsation of an acoustic speech signal. For example, EM sensors can measure tissue wall motions in pharynx, tongue surface, internal and external surfaces of the lips and or nostrils, and neck skin attached to pharynx walls. Such an approach is easier and more accurate than acoustically measuring vibrations of vocal folds.

EM sensor signals from targeted tissue surface-motions, are corrected for sensor response functions, for tissue response functions, and are filtered to remove low frequency noise (typically <200 Hz) to a degree needed for an application. This method provides directional acoustic speech signal acquisition with little external noise contamination.

Transfer Functions

Methods of characterizing a measured acoustic signal over a fixed time frame, using a measured and determined airflow or air pressure excitation function, and an estimated transfer function (or transfer function filter coefficients), are described in U.S. Pat. No. 5,729,694 and U.S. patent application Ser. Nos. 08/597,596 and 09/205,159. Such methods characterize speech accurately, inexpensively, and conveniently. Herein the terms "transfer function," "corresponding filter coefficients" and "corresponding filter function" are used interchangeably.

Figure 4:
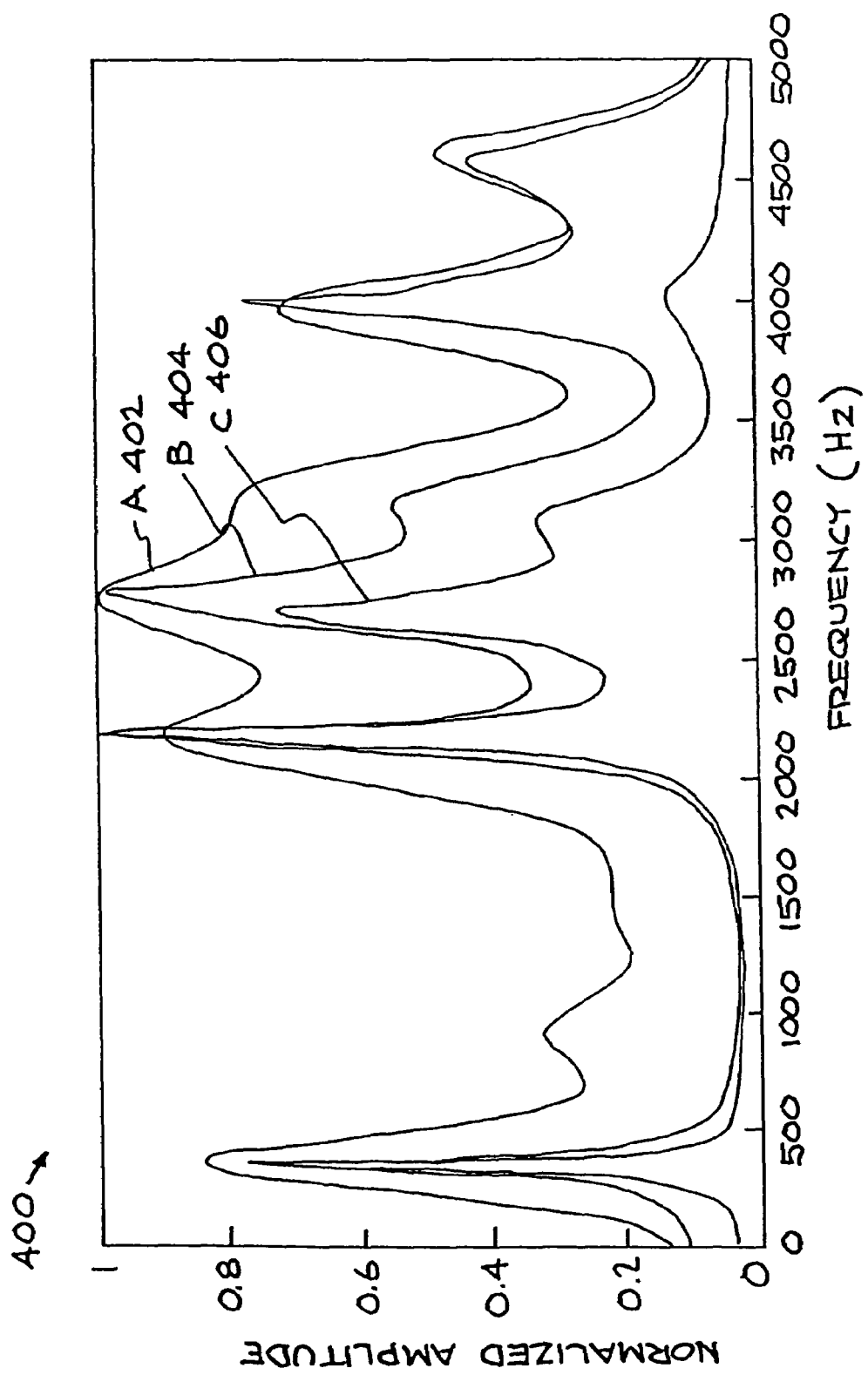
FIG. 4 is a graph of a transfer function obtained for an exemplary "i" sound.

FIG. 4 is a graph 400 of a transfer function 404 obtained by using excitation methods herein for an exemplary "i" sound. The transfer function 404 is obtained using the excitation methods herein and measured acoustic output over a speech unit time frame, for the speech unit /i/, spoken as "eeee." For comparison purposes, curve A 402 is a transfer function for "i" using Cepstral methods, and curve C 406 is a transfer function for "i" using LPC methods.

Curve A 402 is formed by a Cepstral method which uses twenty coefficients to parameterize a speech signal. The Cepstral method does not characterize curve shapes (called "formants") as sharply as the transfer function curve B 404, obtained using the present invention.

Curve C 406 is formed by a fifteen coefficient LPC (linear predictive modeling) technique, which characterizes transfer functions well at lower frequencies (<2200 Hz), but not at higher frequencies (>2200 Hz).

Curve B 404, however, is formed by an EM sensor determined excitation function using methods herein. The transfer function is parameterized using a fifteen pole, fifteen zero ARMA (autoregressive moving average) technique. This transfer function shows improved detail compared to curves 402 and 406.

Good quality excitation function information, obtained using methods herein and those included by reference, accurate time frame definitions, and a measurement of the corresponding acoustic signal enable calculation of accurate transfer-functions and transfer-function-filters. The techniques herein, together with those included by reference, cause the calculated transfer function to be "matched" to the EM sensor determined excitation function. As a result, even if the excitation functions obtained herein are not "perfect," they are sufficiently close approximations to the actual glottal region airflow or air pressure functions, that each voiced acoustic speech unit can be described and subsequently reconstructed very accurately using their matched transfer functions.

Noise Removal

Figure 5:
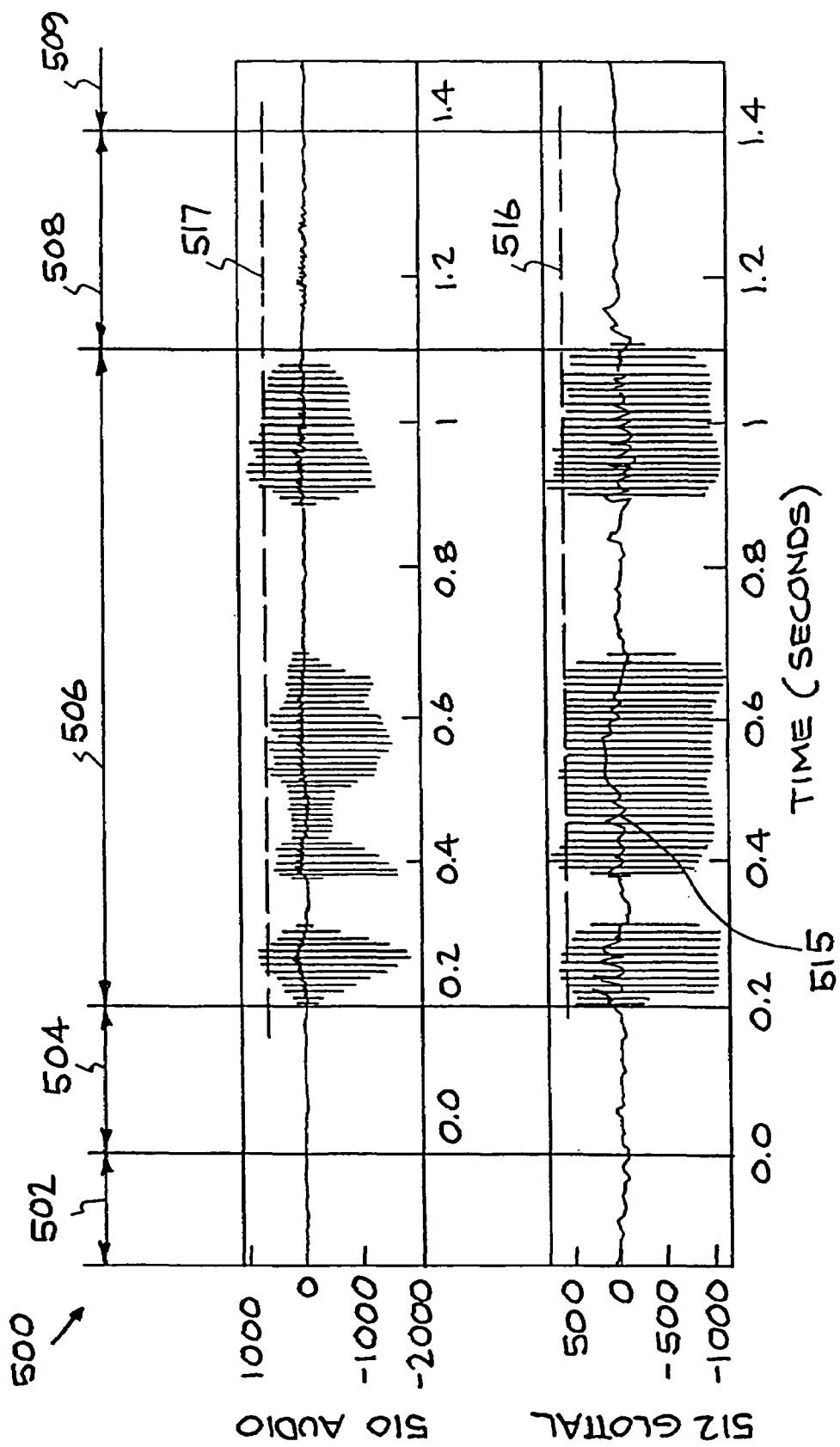
FIG. 5 is a graph of an exemplary speech segment containing a no-speech time period, an unvoiced pre-speech time period, a voiced speech time period, and an unvoiced post-speech time period.

FIG. 5 is a graph of an exemplary speech segment containing a no-speech time frame 502, an unvoiced speech time frame 504, a voiced speech time frame 506, an unvoiced post-speech time frame 508, and a no-speech time frame 509. Timing and other qualities of an acoustic speech signal and an EM sensor signal are also shown. The EM sensor signals provide a separate stream of information relating to the production of acoustic speech. This information is unaffected by all acoustic signals external to the vocal tract of a user. EM sensor signals are not affected by acoustic signals such as machine noise or other speech acoustic sources. EM sensors enable noise removal by monitoring glottal tissue motions, such as, windpipe wall section motions, and they can be used to determine a presence of phonation (including onset, continuity, and ending) and a smoothness of a speech production.

The EM sensors 102 and 104 determine whether vocalization (i.e., opening and closing of the glottis) is occurring, and glottal excitation function regularity. "Regularity" is here defined as the smoothness of an envelope of peak-amplitudes-versus-time of the excitation signals. For example, a glottal radar signal (i.e., EM sensor signal) in time period 506, when vocalization is occurring, has peak-envelope values of about 550±150. These peak values are "regular" by being bounded by approximate threshold values of ±150 above and below an average peak-glottal EM sensor signal 516 with a value of about 550.

Other EM sensors (not shown) can measure other speech organ motions to determine if speech unit transitions are occurring. These EM signals can indicate unvoiced speech production processes or transitions to voiced speech or to no-speech. They can characterize vocal fold retraction, pharynx enlargement, rapid jaw motion, rapid tongue motion, and other vocal tract motions associated with onset, production, and termination of voiced and unvoiced speech segments. They are very useful for determining speech unit transitions when a strong noise background that confuses a speaker's own acoustic speech signal is present.

Four methods for removing noise from unvoiced and voiced speech time frames using EM sensor based methods are discussed in turn below.

First Method for Removing Noise:

Using a first method, noise may be removed from unvoiced and voiced speech by identifying and characterizing noise that occurs before or after identified time periods during which speech is occurring. A master speech onset algorithm, describe in U.S. patent application Ser. No.: 08/597,596, FIG. 19, can be used to determine the no-speech time frame 502 for a predetermined time before the possible onset of unvoiced speech 504 and the no-speech times 509 after the end of unvoiced speech 508. During one or more no-speech time frame s 502, 509 background (i.e., non-user-generated speech) acoustic signals can be characterized. An acoustic signal 510 from the acoustic microphone 126 and a glottal tissue signal 512 from the EM sensor 104 is shown. This first method requires that two statistically determined, language-specific time intervals be chosen (i.e., the unvoiced pre-speech time period 504 and the unvoiced post-speech time period 508. These time frames 504 and 508 respectively describe a time before on-set of phonation and a time after phonation, during which unvoiced speech units are likely to occur.

For example, if time frame 504 is 0.2 seconds and time frame 508 is 0.3 seconds, then a noise characterization algorithm can use a time frame of 0.2 seconds in duration, from 0.4 to 0.2 seconds before the onset of the voicing period 506, to characterize a background acoustic signal. The noise characterization algorithm can also use the no-speech time 509 after speech ends to characterize background signals, and to then compare those background signals to a set of background signals measured in preceding periods (e.g., 502) to determine changes in noise patterns for use by adaptive algorithms that constantly update noise characterization parameters.

Background acoustic signal characterization includes one or more steps of measuring time domain or frequency domain qualities. These can include obtaining an average amplitude of a background signal, peak signal energy and/or power of one or more peak noise amplitudes (i.e. noise spikes) and their time locations in a time frame. Noise spikes are defined as signals that exceed a predetermined threshold level. For frequency domain characterization, conventional algorithms can measure a noise power spectrum, and "spike" frequency locations and bandwidths in the power spectrum. Once the noise is characterized, conventional automatic algorithms can be used to remove the noise from the following (or preceding) speech signals. This method of determining periods of no-speech enables conventional algorithms, such as, spectral subtraction, frequency band filtering, and threshold clipping to be implemented automatically and unambiguously.

Method 1 of noise removal can be particularly useful in noise canceling microphone systems where noise reaching a $2^{nd}$, noise-sampling microphone and slightly different noise reaching a speaker's microphone, can be unambiguously characterized every few seconds, and used to cancel background noise from speaker speech signals.

Figure 6:
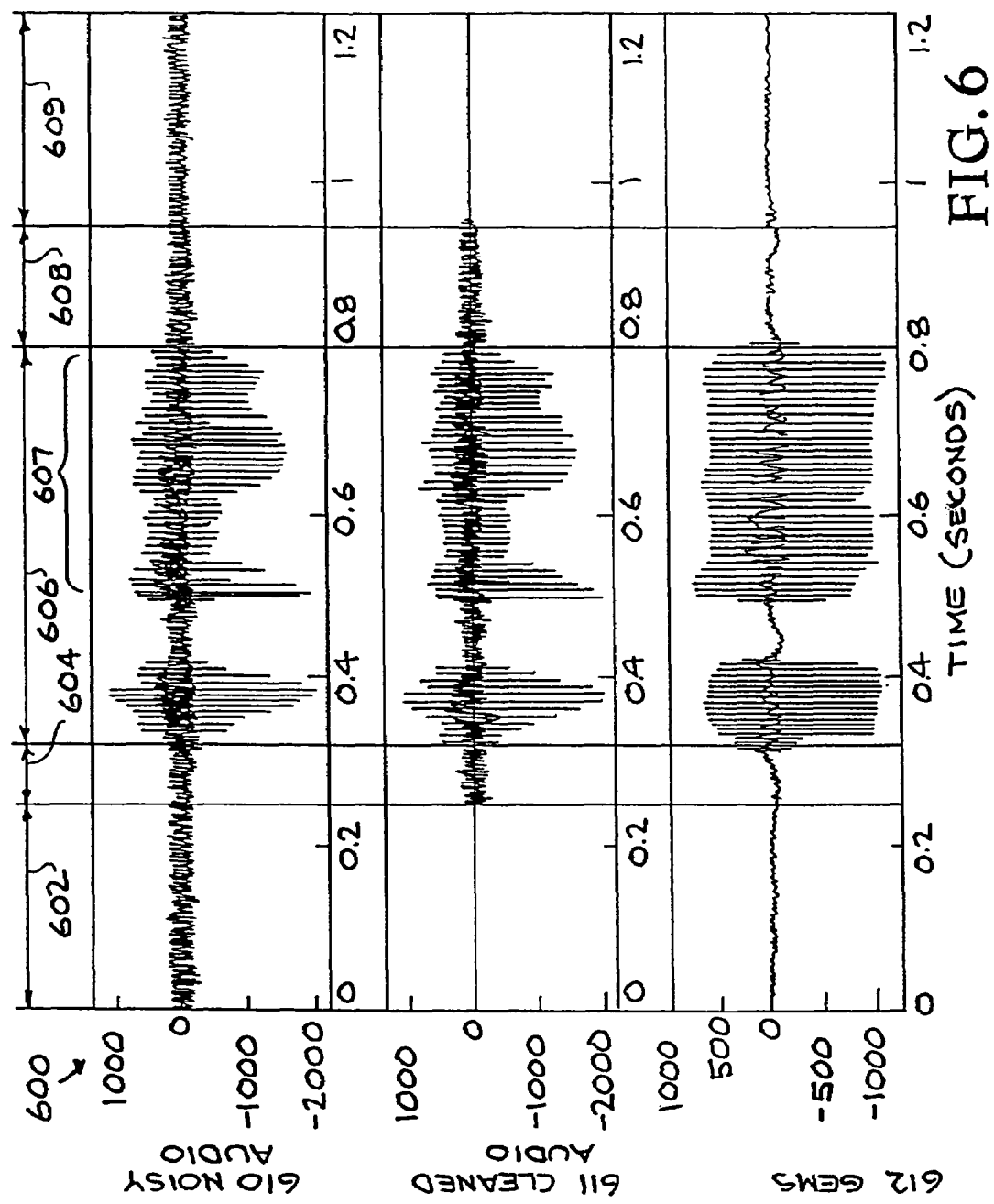
FIG. 6 is a graph of an exemplary acoustic speech segment mixed with white noise, and an exemplary EM signal.

Second Method for Removing Noise:

FIG. 6 is a graph 600 of an exemplary acoustic speech segment 610 mixed with white noise. Also shown are a set of no-speech 602, 609 frames, a set of unvoiced 604, 608 speech frames, and several voiced frames 606, and an exemplary EM signal 612. Using the method of no-speech period detection described above and by reference, the noise signal can be subtracted from the acoustic signals that occur during the time frames of the no-speech 602, 698. This results in signal 611. This process reduces average noise on the signal, and enables automatic speech recognizers to turn on and turn off automatically.

For voiced speech periods 606, "averaging" techniques can be employed to remove random noise from signals during a sequence of time frames of relatively constant voiced speech, whose timing and consistency are defined by reference. Voiced speech signals are known to be essentially constant over two to ten glottal time frames. Thus an acoustic speech signal corresponding to a given time frame can be averaged with acoustic signals from following or preceding time frames using very accurate timing procedures of these methods, and which are not possible using conventional all-acoustic methods. This method increases a signal to noise ratio approximately as $(N)^{1/2}$, where N is a number of time frames averaged.

Another method enabled by methods herein is impulse noise removal.

Figure 7:
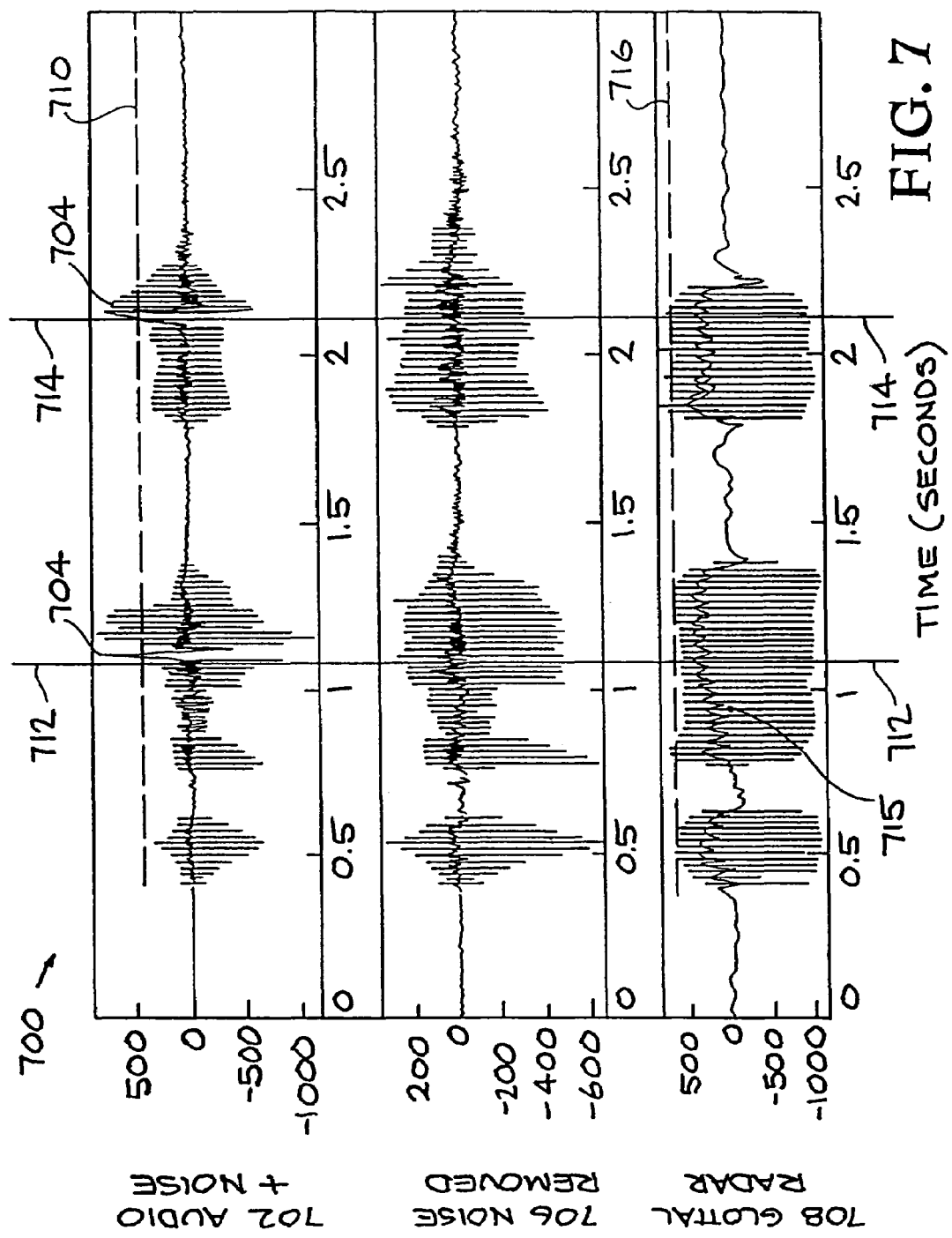
FIG. 7 is a graph of an exemplary acoustic speech segment with periodic impulsive noise, an exemplary acoustic speech segment with noise replaced, and an exemplary EM signal.

FIG. 7 is a graph 700 of an exemplary acoustic speech segment 702 with a periodic impulsive noise 704 an exemplary acoustic speech segment with noise replaced 706, and an exemplary EM sensor signal 708. During voiced or unvoiced speech periods, impulse noise 704 is defined as a signal with an amplitude (or other measure) which exceeds a predetermined value. Continuity of the EM glottal sensor signal enables removal of noise spikes from an acoustic speech signal. Upon detection of an acoustic signal that exceeds a preset threshold 710 (e.g., at times $T_{N1}$ 712 and $T_{N2}$ 714) the EM sensor signal 708 is tested for any change in level that would indicate a significant increase in speech level. Since no change in the EM sensor signal 708 is detected in FIG. 7, the logical decision is: the acoustic signal that exceeds the preset threshold, is corrupted by noise spikes. The speech signal over those time frames that are corrupted by noise, are corrected by first removing the acoustic signal during the speech time frames. The removed signal is replaced with an acoustic signal from a preceding or following time frame 715 (or more distant time frames) that have been tested to have signal levels below a threshold and with a regular EM sensor signal. The acoustic signal may also be replaced by signals interpolated using uncorrupted signals, from frames preceding and following the corrupted time frame. A threshold level for determining corrupted speech can be determined in several additional ways that include, using two thresholds to determine continuity, a first threshold obtained by using a peak envelope value of short time acoustic speech-signals 517, averaged over the time frame 506, and a second threshold using a corresponding short time peak envelope value of the EM sensor signal 516, averaged over the time frame 506. Other methods use frequency amplitude thresholds in frequency space, and several other comparison techniques are possible using techniques known to those skilled in the art.

A method of removing noise during periods of voiced speech is enabled using EM-sensor-determined excitation functions. A power spectral density function of an excitation function (defined over a time frame determined using an EM sensor) defines passbands of a filter that is used to filter voiced speech, while blocking a noise signal. This filter can be automatically constructed for each glottal cycle, or time frames of several glottal cycles, and is then used to attenuate noise components of spectral amplitudes of corresponding mixed speech plus noise acoustic signal.

Figure 8A:
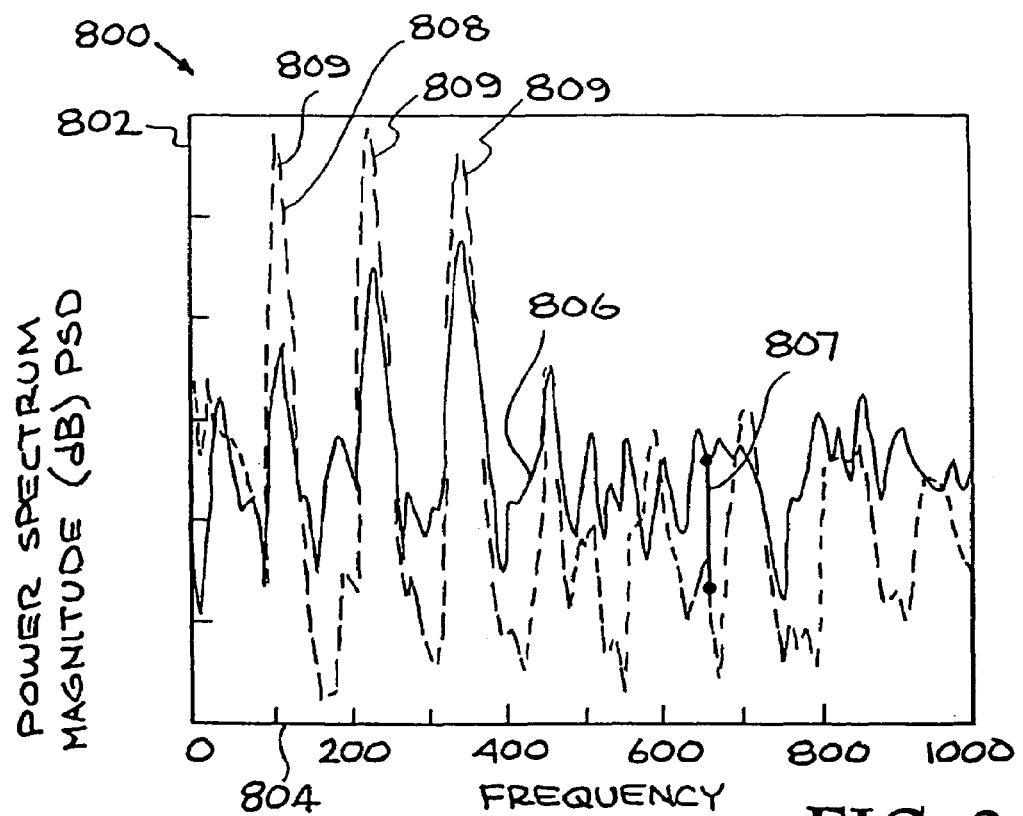
FIG. 8A is a graph of a power spectral density verses frequency of a noisy acoustic speech segment and a filtered acoustic speech segment.

FIG. 8A is a graph 800 of a power spectral density 802 versus frequency 804 of a noisy acoustic speech segment 806 and a filtered acoustic speech segment 808 using the method in the paragraph above. The noisy acoustic speech signal is an acoustic speech segment mixed with white noise—3 db in power compared to the acoustic signal. The noisy speech segment 806 is for an /i/ sound, and was measured in time over five glottal cycles. A similar, illustrative noisy speech acoustic signal 610 and corresponding EM signal 612 occur together over time frame 607 of voiced speech.

This filtering algorithm first obtains a magnitude of a Fast Fourier Transform (FFT) of an excitation function corresponding to an acoustic signal over a time frame, such as five glottal cycles. Next, it multiplies the magnitude of the FFT of the excitation function, point by point, by the magnitude of the FFT of the corresponding noisy acoustic speech signal (e.g., using magnitude angle representation) to form a new "filtered FFT amplitude." Then the filtering algorithm reconstructs a filtered acoustic speech segment by transforming the "filtered FFT amplitude" and the original corresponding FFT polar angles (of the noisy acoustic speech segment) back into a time domain representation, resulting in a filtered acoustic speech segment. This method is a correlation or "masking" method, and works especially well for removing noise from another speaker's speech, whose excitation pitch is different than that of a user.

Figure 8B:
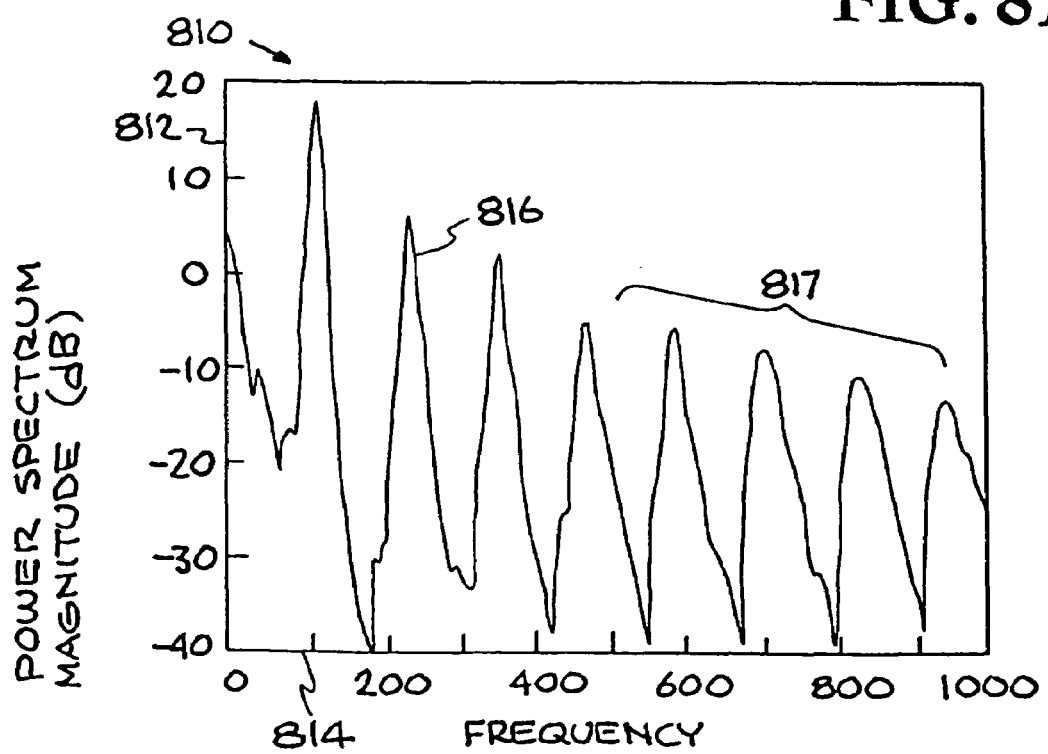
FIG. 8B is a graph of power spectral density verses frequency of an exemplary EM sensor signal used as an approximate excitation function.

FIG. 8B shows an illustrative example graph 810 of power spectral density 816 verses frequency of the EM sensor signal corresponding to the speech plus noise data in FIG. 8A, 806. The EM sensor signal was converted to a voiced excitation function using excitation method 1. Higher harmonics of the excitation function 817 are also shown. The filtering takes place by multiplying amplitudes of excitation signal values 816 by amplitudes of corresponding noisy acoustic speech values 806 (point by point in frequency space). In this way the "filtered FFT amplitude" 808 is generated. For frequencies consistent with those of the excitation function, the "filtered FFT amplitude" is enhanced by this procedure (see dotted signal peaks 809 at frequencies 120, 240, and 360 Hz) compared to a signal value 806 at the same frequencies. At other speech plus noise signal values 806 (e.g., the solid line at 807), that are not consistent with excitation frequencies, the corresponding "filtered FFT amplitude" value is reduced in amplitude by the filtering.

Other filtering approaches are made possible by this method of voiced-speech time-frame filtering. An important example is to construct a "comb" filter, with unity transmission at frequencies where an excitation function has significant energy, e.g., within its 90% power points, and setting transmission to be zero elsewhere, and other procedures known to these skilled in the art. Another important approach of noise removal method 2 is to use model-based filters (e.g., Kalman filters) that remove signal information that does not meet the model constraints. Model examples include expected frequency domain transfer functions, or time domain impulse response functions.

Third Method for Removing Noise:

Using a third method, echo and feedback noise may be removed from unvoiced and voiced speech.

Figure 9:
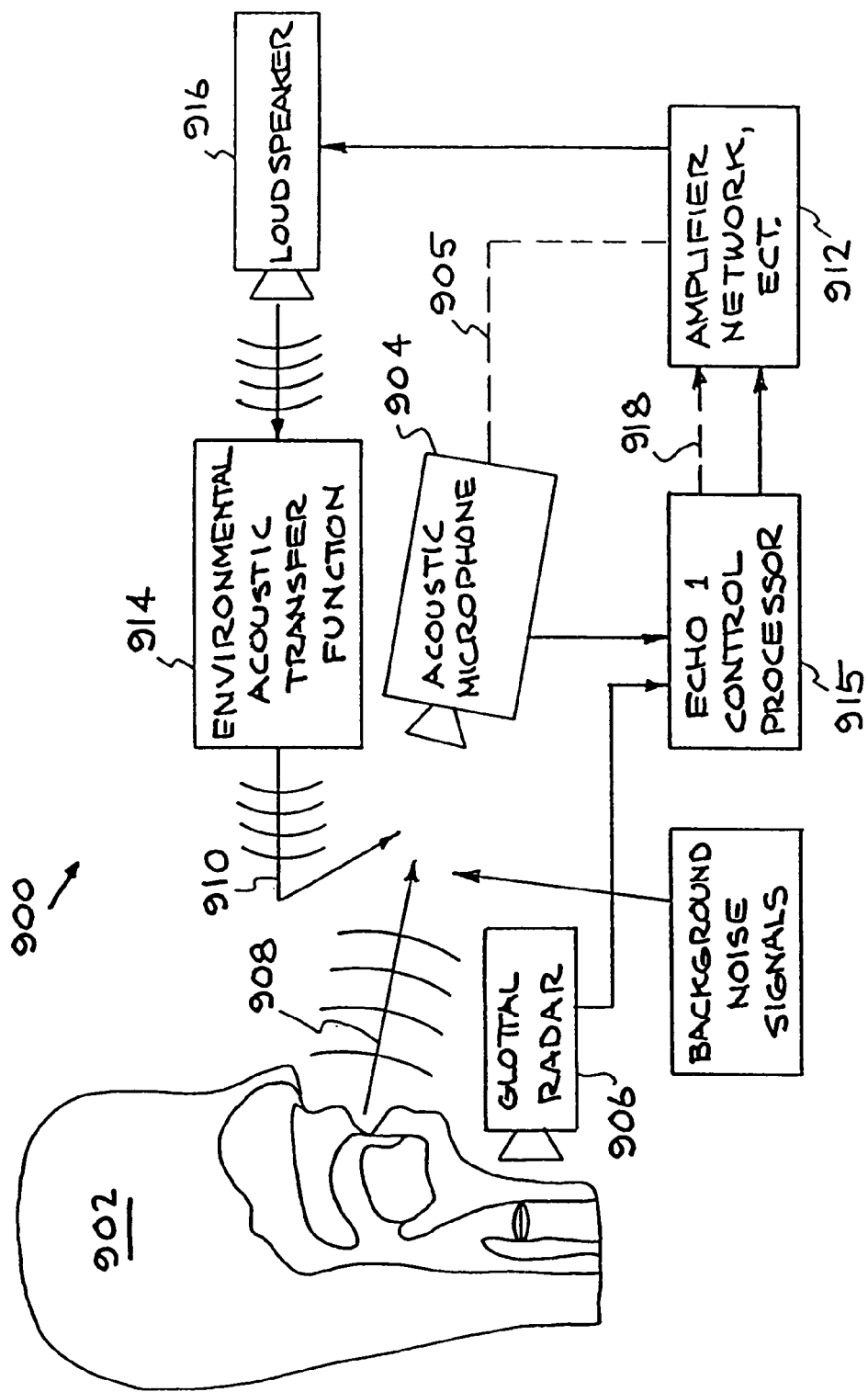
FIG. 9 is a dataflow diagram of a sound system feedback control system.

FIG. 9 illustrates elements of an echo producing system 900. Echoes and feedback often occur in electronic speech systems such as public address systems, telephone conference systems, telephone networks, and similar systems. Echoes and feedback are particularly difficult to remove because there has been no automatic way to reliably measure speech onset, speech end, and echo delay. A first type of echo and feedback, herein named Echo1, is a partial replica 910 of a speech signal 908, in which a particular frequency or frequency band of sound is positively amplified by a combination of an environment acoustic transfer function 914, an electronic amplification system 912, and by a loudspeaker system 916. Echo1 signals often become self-sustaining and can grow rapidly, by a positive feedback loop in their electronics and environment. These are heard commonly in public address systems when a "squeal" is heard, which is a consequence of a positive growing instability. A second method for removing a different type of echoes, named Echo2, is discussed below. Echo2 is a replica of a speech segment that reappears later in time, usually at a lower power level, often in telephone systems.

For Echo1 type signals the method of excitation continuity described above in noise removal method 2, automatically detects an unusual amplitude increase of an acoustic signal over one or more frequencies of the acoustic system 912, 914, 916 over a predetermined time period. A preferred method for control of Echo1 signals involves automatically reducing gain of the electronic amplifier and filter system 912, in one or more frequency bands. The gain reduction is performed using negative feedback based upon a ratio of an average acoustic signal amplitude (averaged over a predetermined time frame) compared to the corresponding averaged excitation function values, determined using an EM glottal sensor 906. Typically 0.05–1.0 second averaging times are used.

The Echo1 algorithm first uses measured acoustic spectral power, in a signal from an acoustic microphone 904, and in a glottal signal from the EM sensor (e.g. glottal radar) 906, in several frequency bands. The rate of acoustic and EM sensor signal-level sampling and algorithm processing must be more rapid than a response time of the acoustic system 912, 914, 916. If processor 915 measures a more rapid increase in the ratio of acoustic spectral power (averaged over a short time period) in one or more frequency bands, compared to the corresponding voiced excitation function (measured using the EM sensor 906) then a feedback signal 918 can be generated by the processor unit 915 to adjust the gain of the electronic amplifier system 912, in one or more filter bands. Acceptable rate of change values and feedback qualities are predetermined and provided to the processor 915. In other words, the acoustic system can be automatically equalized to maintain sound levels, and to eliminate uncontrolled feedback. Other methods using consistency of expected maximum envelope values of the acoustic and EM sensor signal values together, can be employed using training techniques, adaptive processing over periods of time, or other techniques known to those skilled in the art.

Removal of Echo2 acoustic signals is effected by using precise timing information of voiced speech, obtained using onset and ending algorithms based upon EM sensors herein or discussed in the references. This information enables characterization of acoustic system reverberation, or echoes timing.

Figure 10:
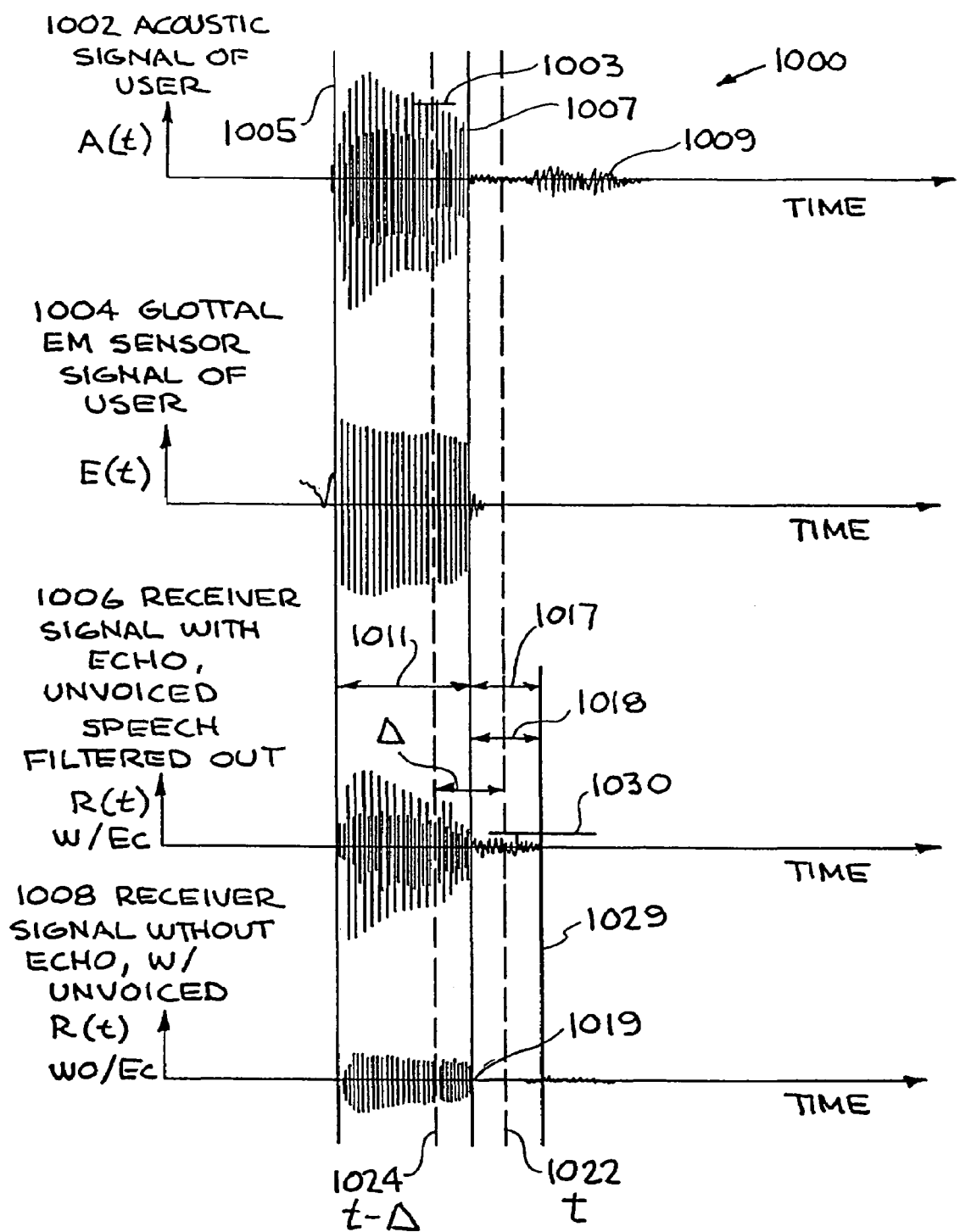
FIG. 10 is a graph of two exemplary methods for echo detection and removal in a speech audio system using an EM sensor.

FIG. 10 is a graph 1000 of an exemplary method for echo detection and removal in a speech audio system using an EM sensor. First, a presence of an echo is detected in a time period following an end of voiced speech, 1007, by first removing unvoiced speech by low-pass filtering (e.g., <500 Hz) an acoustic signal in voiced time frame 1011 and echo frame 1017. An algorithm tests for presence of an echo signal, following the voiced speech end-time 1007, that exceeds a predetermined signal, and finds an end time 1020 for the echo signal. The end-time of the voiced speech during time frame 1011 is obtained using EM sensor signal 1004, and algorithms discussed in the incorporated references. These EM sensor based methods can be especially useful for telephone and conference calls where sound in a receiver 1006 is a low-level replica of both a speaker's present time voice (from 1002) plus an echo of his or her past speech signal 1017, delayed by a time delta $\Delta$, 1018. Note that echoes caused by initial speech can overlap both the voiced frame 1011 and the echo frame 1017, which can contain unvoiced signals, as well as echoes.

Since common echoes are usually one second or less in delay, each break in voiced speech, one second or longer, can be used to re-measure an echo delay time of the electronic/acoustic system being used. Such break times can occur every few seconds in American English. In summary, by obtaining the echo delay time 1018, using methods herein, a cancellation filter can be automatically constructed to remove the echo from the acoustic system by subtraction.

An exemplary cancellation filter algorithm works by first storing sequentially signal values A(t), from a time sequence of voiced speech in time frame 1011 followed by receiver signals R(t) in time frame 1017, in a new combined time frame in a short term memory. In this case, speech signals R(t) 1006 in time frame 1017 include echo signals Ec(t) 1030 as well as unvoiced signals. The sequence of signals in the short term memory is filtered by a low pass filter, e.g, <500 Hz. These filtered signals are called A' and Ec' and their corresponding time frames are noted as 1011' and 1017'. These two time frames make a combined time frame in the short term memory. First, the algorithm finds an end time of the voiced signal 1007 using EM sensor signal 1004; the end time of the voiced signal is also same as time 1007'. Then the algorithm finds an end time 1020' of echo signal Ec' by determining when the signal Ec' falls below a predetermined threshold. Delta, $\Delta$, is defined to be 1007'+$\Delta$=1020'. Next an algorithm selects a first time "t" 1022' from the filtered time frame 1017', and obtains a corresponding acoustic signal sample A'(t–$\Delta$), at an earlier time, t–$\Delta$, 1024'. A ratio "r" is then formed by dividing filtered echo signal Ec'(t) measured at time "t" 1022' by the filtered speaker's acoustic signal A'(t–$\Delta$) 1024'. An improved value of "r" can be obtained by averaging several signal samples of the filtered echo level Ec'($t_i$), at several times $t_i$, in time frame 1017', and dividing said average by correspondingly averaged signals A'($t_i$–$\Delta$). Filtered values A(t) and R(t) are used to remove unvoiced speech signals from the echoes signal Ec(t) which can otherwise make finding the echo amplitude ratio "r" more difficult.

$$r = Ec'(t)/A'(t-\Delta) \quad \text{(eqn: E2-1)}$$

Filtered receiver acoustic signal values R'(t) 1030 at times t', in frame 1017', have echo signals removed by subtracting adjusted values of earlier filtered acoustic signals A'(t–Δ), using ratio "r" determined above. To do this, each speech signal value A'(t–Δ) 1002' is adjusted to a calculated (i.e., expected) echo value Ec'(t) by multiplying A'(t–Δ) times the ratio r:

$$A'(t-\Delta) \times r = \text{calculated echo value, } Ec'(t) \quad \text{(eqn: E2-2)}$$

The echo is removed from signal R'(t) in time frame 1017' leaving a residual echo signal 1019 in the time-frame following voiced speech 1017:

$$\text{Residual-echo } Er(t) = Ec'(t) - A'(t-\Delta) \times r \quad \text{(eqn: E2-3)}$$

Because echoes are often inverted in polarity upon being generated by the electronic system, an important step is to determine if residual values are actually smaller than the receiver signal 1006' at time t. Human ears do not usually notice this sign change, but the comparison algorithm being described herein does require polarity to be correct:

$$\text{Is "} Er'(t) < R'(t) \text{"?} \quad \text{(eqn: E2-4)}$$

If "no", then the algorithm changes a negative sign between the symbols R'(t) and A'(t–Δ), "–", in equation E2-3 above to "+", and recalculates the residual Er'(t). If "yes", then the algorithm can proceed to reduce the echo residual value obtained in E2-3 further, or proceed using Δ from the initial algorithm test.

To improve Δ, one or more echo signals Ec'(t) in time 1017' are chosen. An algorithm varies time delay value Δ, minimizing equation E2-3 by adding and subtracting small values of one or more time steps (within a predetermined range), and finds a new value Δ' to use in E2-3 above. A value Δ' that minimizes an echo residual signal for one or more times t in the short term time frame following the end of voiced speech 1007, is a preferred delay time Δ to use.

The algorithm freezes "r" and Δ, and proceeds to remove, using equation E2-3, the echo signal from all values of R(t) for all t, which have an potential echo caused by a presence of an unvoiced or voiced speech signal that has occurred at a time t–Δ earlier than a time of received signal R(t).

Synthesized Speech

Figure 11A:
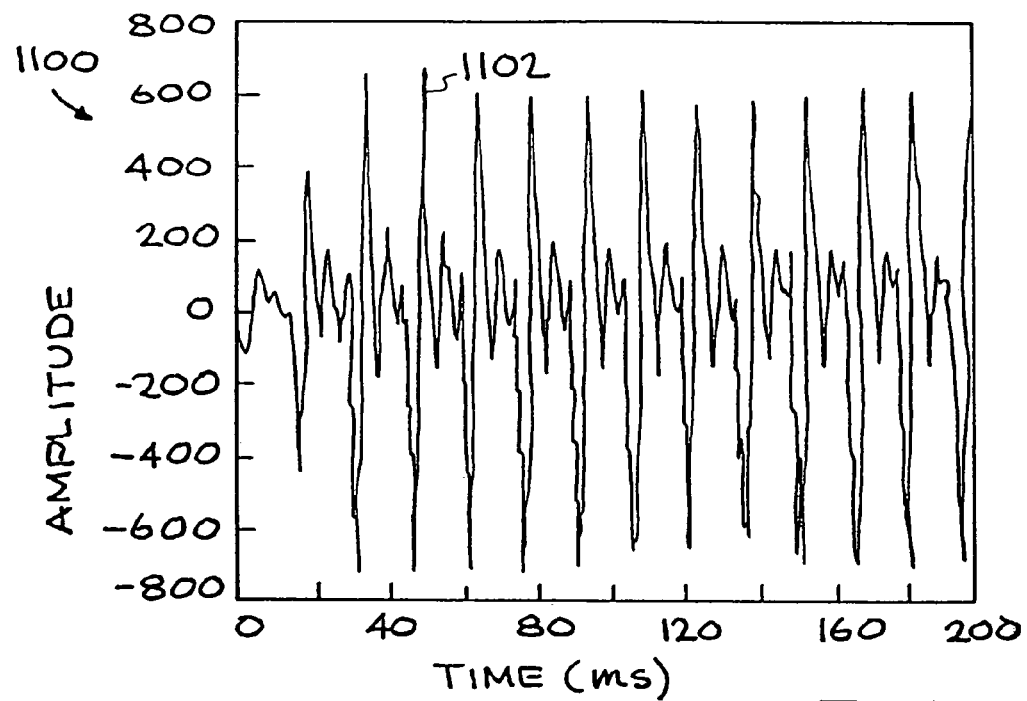
FIG. 11A is a graph of an exemplary portion of recorded audio speech.
Figure 11B:
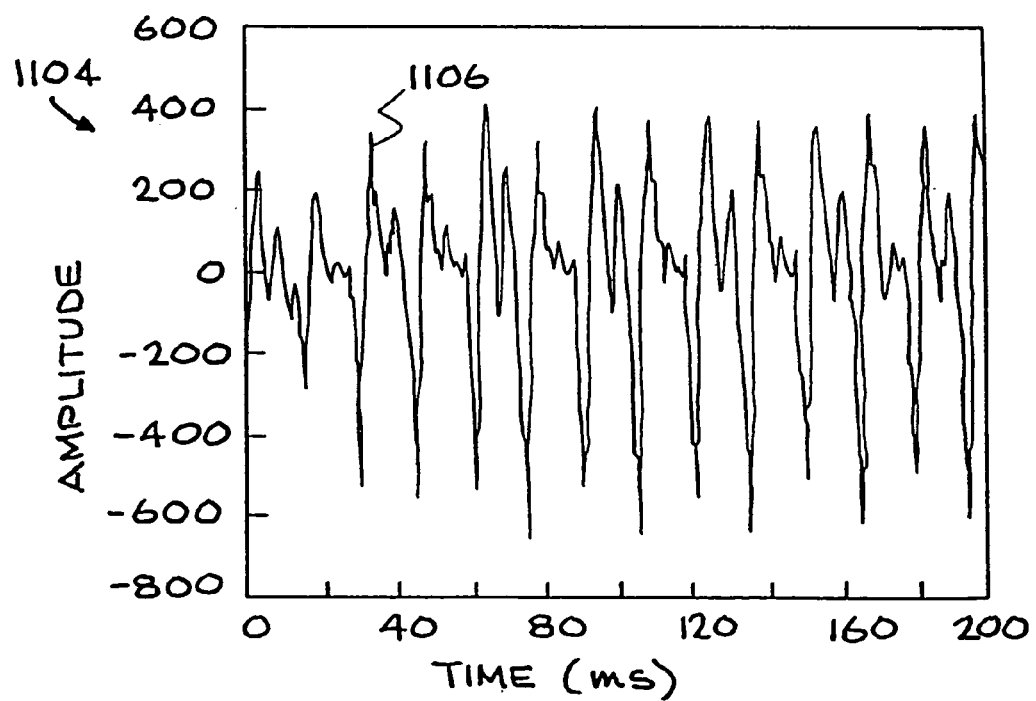
FIG. 11B is a graph of an exemplary portion of synthesized audio speech according to the present invention.

Referring to FIG. 11A, a graph 1100 of an exemplary portion of recorded audio speech 1102 is shown, and in FIG. 11B, a graph 1104 of an exemplary portion of synthesized audio speech 1106 is shown. This synthesized speech segment 1104 is very similar to the directly recorded segment 1102, and sounds very realistic to a listener. The synthesized audio speech 1106 is produced using the methods of excitation function determination described herein, and the methods of transfer function determination, and related filter function coefficient determination, described in U.S. patent application Ser. No. 09/205,159 and U.S. Pat. No. 5,729, 694.

A first reconstruction method convolves Fast Fourier Transforms (FFTs) of both an excitation function and a transfer function to obtain a numerical output function. The numerical output function is FFT transformed to a time domain and converted to an analog audio signal (not shown in Figures).

The second reconstruction method (shown in FIG. 11B) multiplies the time domain excitation function by a transfer function related filter, to obtain a reconstructed acoustic signal 1106. This is a numerical function versus time, which is then converted to an analog signal. The excitation, transfer, and residual functions that describe a set of speech units in a given vocabulary, for subsequent synthesis, are determined using methods herein and in those incorporated by reference. These functions, and/or their parameterized approximation functions are stored and recalled as needed to synthesize personal or other types of speech. The reconstructed speech 1106 is substantially the same as the original 1102, and it sounds natural to a listener. These reconstruction methods are particularly useful for purposes of modifying excitations for purposes of pitch change, prosody, and intonation in "text to speech" systems, and for generating unusual speech sounds for entertainment purposes.

Figure 12:
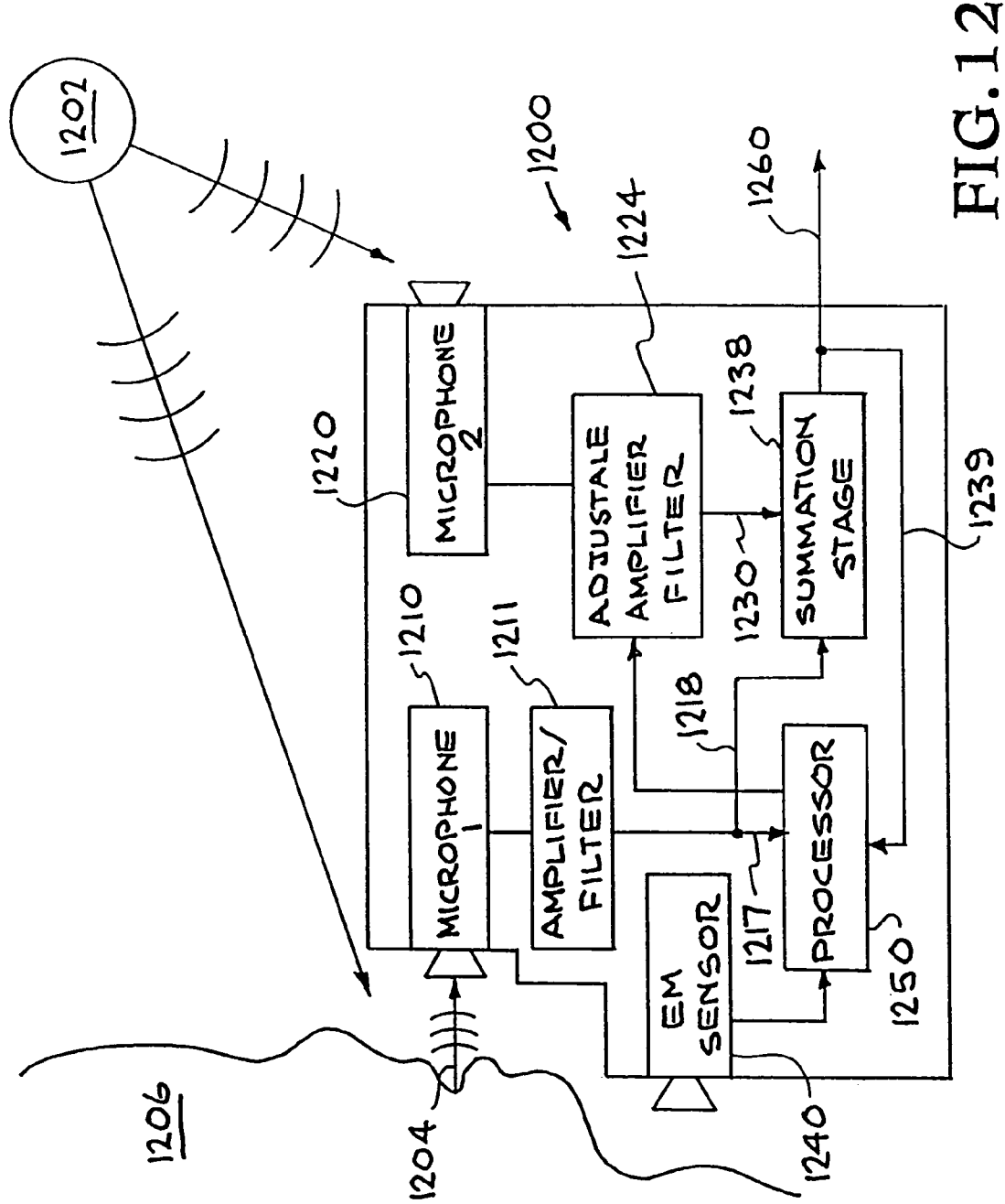
FIG. 12 is a pictorial diagram of an exemplary EM sensor, noise canceling microphone system.

EM Sensor Noise Canceling Microphone:

FIG. 12 is a pictorial diagram of an exemplary EM sensor, noise canceling microphone system 1200. This system removes background acoustic noise from unvoiced and voiced speech, automatically and with continuous calibration. Automated procedures for defining time-periods during which background noise can be characterized, are described above in "Noise removal Method 1" and the incorporated by reference documents. Use of an EM sensor to determine no-speech time periods allows acoustic systems, such as noise canceling microphones, to calibrate themselves. During no-speech periods, a processor 1250 uses user microphone 1210 and microphone 1220 to measure background noise 1202. Processor 1250 compares output signals from the two microphones 1210 and 1220 and adjusts a gain and phase of output signal 1230, using amplifier and filter circuit 1224, so as to minimize a residual signal level in all frequency bands of signal 1260 output from a summation stage 1238. In the summation stage 1238 the amplified and filtered background microphone signal 1230 is set equal and opposite in sign to a speaker's microphone signal 1218 by the processor 1250, using feedback 1239 from the output signal 1260.

Cancellation values determined by circuit 1224 are defined during periods of no-speech, and frozen during periods of speech production. The cancellation values are then re-determined at a next no-speech period following a time segment of speech. Since speech statistics show that periods of no-speech occur every few seconds, corrections to the cancellation circuit can be made every few seconds. In this manner the cancellation microphone signal can be adapted to changing background noise environments, changing user positioning, and to other influences. For those conditions where a substantial amount of speech enters microphone 1220, procedures similar to above can be employed to ensure that this speech signal does not distort primary speech signals received by the microphone 1210.

Multi Organ Method of Measurement

Figure 13:
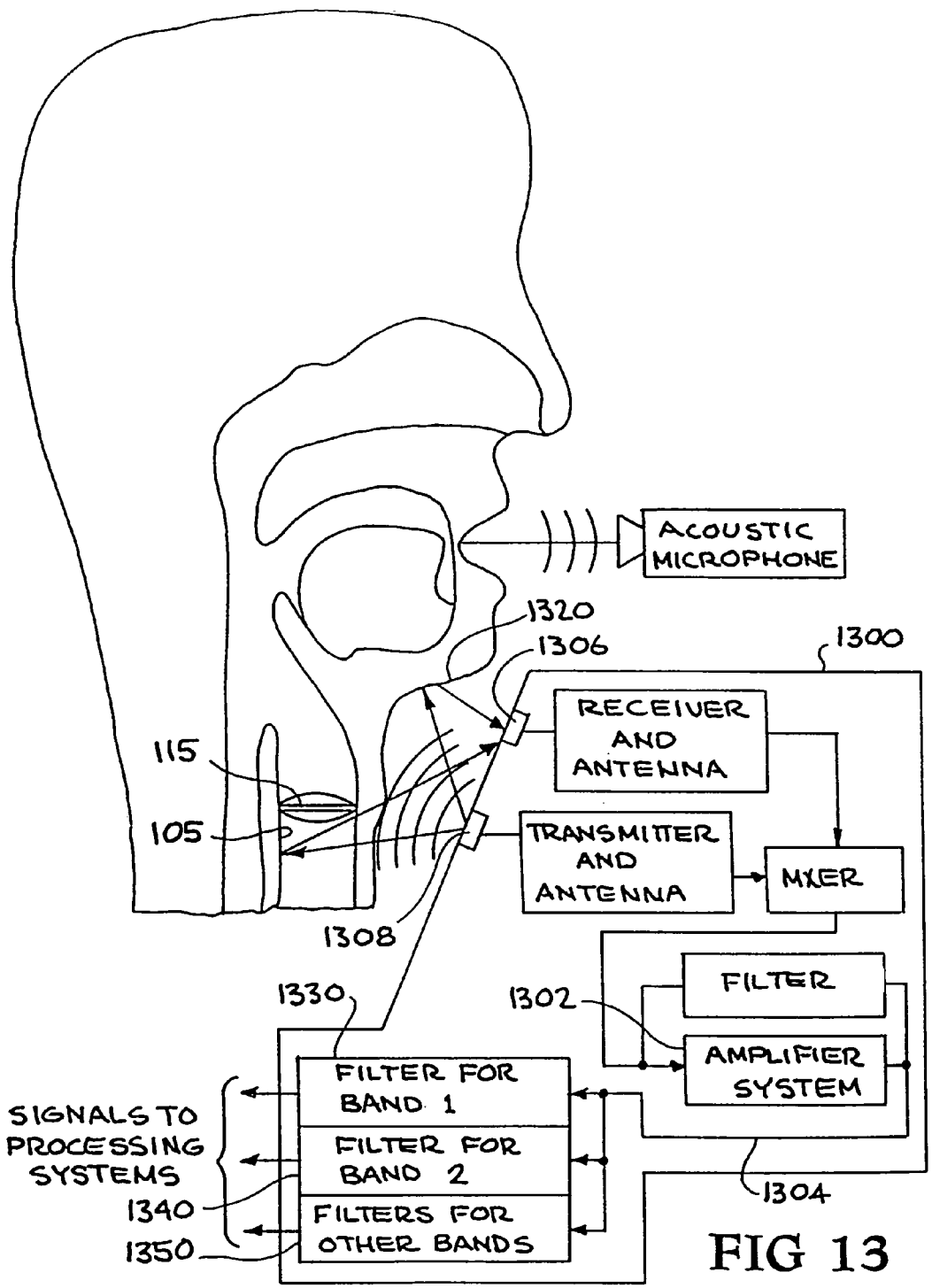
FIG. 13 is a block diagram of a multi-articulator EM sensor system.

FIG. 13 is a block diagram of a multi-band EM sensor 1300 system that measures multiple EM wave reflections versus time. The EM sensor system 1300 provides time domain information on two or more speech articulator systems, such as sub-glottal rear wall 105 motion and jaw up/down motion 1320, in parallel. One frequency filter 1330 is inserted in an output 1304 of EM sensor amplifier stage 1302. A second filter 1340 is inserted also in the output 1304. Additional filters 1350 can be added. Each filter generates a signal whose frequency spectrum (i.e., rate of change of position) is normally different from other frequency spectrums, and each is optimized to measure a given speech organ's movement versus time. In a preferred embodiment, one such filter 1330 is designed to present tracheal wall 105 motions from 70 to 3000 Hz and a second filter 1340 output provides jaw motion from 1.5 Hz to 20 Hz. These methods are easier to implement than measuring distance differences between two or more organs using range gate methods.

In many cases, one or more antennas 1306, 1308 of the EM sensor 1300, having a wide field of view, can detect changes in position versus time of air interface positions of two or more articulators.

The filter electronics 1330, 1340, 1350 commonly become part of the amplifier/filter 1302, 1303 sections of the EM sensor 1300. The amplifier system can contain operational amplifiers for both gain stages and for filtering. Several such filters can be attached to a common amplified signal, and can generate amplified and filtered signals in many pass bands as needed.

While one or more embodiments of the present invention have been described, those skilled in the art will recognize that various modifications may be made. Variations upon and modifications to these embodiments are provided by the present invention, which is limited only by the following claims.

What is claimed is:

1. A method for removing acoustic noise from an acoustic speech signal, comprising the steps of:

producing EM waves using an EM sensor;

selecting a first set of acoustic speech time frames with timing defined by an excitation function determined using said EM sensor;

characterizing qualities of an acoustic noise signal over a second set of time frames with timing defined by an excitation function determined using said EM sensor and by using the acoustic speech signal over said second set of time frames;

constructing an acoustic noise filter appropriate to the acoustic speech signal over the first set of time frames and to the characterized noise signal over the second set of time frames; and filtering the acoustic noise signal from the acoustic speech signal over the first set of time frames using the acoustic noise filter.

2. The method of claim 1, wherein:

the characterizing step includes the step of characterizing the qualities of the acoustic noise signal over the first set of time frames; and the constructing step includes the step of constructing the acoustic noise filter using both acoustic speech signal and noise signal information over the first set of time frames.

3. The method of claim 1 wherein the characterizing step includes the step of characterizing the qualities of the acoustic noise signal over a predetermined portion of a no-speech time period.

* * * * *